(12) United States Patent
Gilboa-Geffen et al.

(10) Patent No.: US 10,835,897 B2
(45) Date of Patent: Nov. 17, 2020

(54) PORTABLE ALLERGEN DETECTION SYSTEM

(71) Applicant: DOTS Technology Corp., Natick, MA (US)

(72) Inventors: Adi Gilboa-Geffen, Wayland, MA (US); Renuka Babu Brown, Weston, MA (US); John H. Kepler, Lexington, MA (US); Gaurav Rohatgi, Waltham, MA (US); Philip Charles Walker, Concord, MA (US); Mark Bates, Westwood, MA (US); Christopher James Page, Cambridge, MA (US)

(73) Assignee: DOTS TECHNOLOGY CORP., Natick, MA (US)

( * ) Notice: Subject to any disclaimer, the term of this patent is extended or adjusted under 35 U.S.C. 154(b) by 263 days.

(21) Appl. No.: 15/705,328

(22) PCT Filed: Mar. 15, 2016

(86) PCT No.: PCT/US2016/022441
§ 371 (c)(1),
(2) Date: Sep. 15, 2017

(87) PCT Pub. No.: WO2016/149253
PCT Pub. Date: Sep. 22, 2016

(65) Prior Publication Data
US 2018/0154350 A1    Jun. 7, 2018

Related U.S. Application Data

(60) Provisional application No. 62/182,900, filed on Jun. 22, 2015, provisional application No. 62/133,632, filed on Mar. 16, 2015.

(51) Int. Cl.
*B01L 3/00* (2006.01)
*B01L 1/00* (2006.01)
(Continued)

(52) U.S. Cl.
CPC ............. *B01L 3/502* (2013.01); *G01N 1/08* (2013.01); *G01N 1/286* (2013.01); *G01N 33/02* (2013.01);
(Continued)

(58) Field of Classification Search
CPC ................................ B01L 3/50; B01L 3/502
See application file for complete search history.

(56) References Cited

U.S. PATENT DOCUMENTS

| 5,976,895 | A | * | 11/1999 | Cipkowski | A61B 10/007 |
|---|---|---|---|---|---|
| | | | | | 422/412 |
| 5,981,287 | A | | 11/1999 | Sinclair et al. | |
| 6,032,368 | A | * | 3/2000 | Huang | A47J 25/00 |
| | | | | | 30/113.1 |
| 6,398,402 | B1 | | 6/2002 | Thomas et al. | |

(Continued)

FOREIGN PATENT DOCUMENTS

WO    2012078455 A1    6/2012

OTHER PUBLICATIONS

International Search Report and Written Opinion dated Jun. 9, 2016 in Application No. PCT/US2016/022441, entitled: Sortable Allergen Detection System.

*Primary Examiner* — Nathan A Bowers
(74) *Attorney, Agent, or Firm* — DT Ward, PC; Donna T. Ward; Lingyun Jia

(57) ABSTRACT

The present invention provides systems, devices and methods for detecting the presence and/or absence of one or more allergens in a sample particularly a food sample. The detection system includes a separate sample pickup, one or more disposables for receiving and processing a test sample and a detection device that can execute an allergen detection testing in minutes. The present detection system and device is compact and portable.

30 Claims, 18 Drawing Sheets

(51) Int. Cl.
*G01N 33/02* (2006.01)
*G01N 1/08* (2006.01)
*G01N 1/28* (2006.01)
*G01N 33/53* (2006.01)
*C12Q 1/6804* (2018.01)

(52) U.S. Cl.
CPC .... *G01N 33/5308* (2013.01); *B01L 2200/025* (2013.01); *B01L 2200/026* (2013.01); *B01L 2200/0605* (2013.01); *B01L 2200/0689* (2013.01); *B01L 2300/042* (2013.01); *B01L 2300/047* (2013.01); *B01L 2300/0609* (2013.01); *B01L 2300/0654* (2013.01); *B01L 2300/0681* (2013.01); *B01L 2300/0867* (2013.01); *B01L 2300/1822* (2013.01); *B01L 2300/1827* (2013.01); *B01L 2400/049* (2013.01); *B01L 2400/0487* (2013.01); *B01L 2400/0694* (2013.01); *C12Q 1/6804* (2013.01); *G01N 2001/2866* (2013.01)

(56) References Cited

U.S. PATENT DOCUMENTS

| | | | |
|---|---|---|---|
| 6,440,373 B1* | 8/2002 | Gomes | B01L 3/508 422/547 |
| 8,211,715 B1 | 7/2012 | Royds | |
| 8,852,922 B2 | 10/2014 | Glezer et al. | |
| 2004/0007387 A1* | 1/2004 | Bar-Cohen | E21B 7/24 175/50 |
| 2010/0137163 A1 | 6/2010 | Link et al. | |
| 2010/0210033 A1* | 8/2010 | Scott | G01N 33/58 436/501 |
| 2012/0088232 A1 | 4/2012 | Wanekaya et al. | |
| 2012/0115211 A1* | 5/2012 | Ajmal | B01L 3/502 435/287.1 |
| 2012/0264232 A1 | 10/2012 | Kramer et al. | |
| 2014/0112844 A1* | 4/2014 | Nee | B01L 3/502 422/557 |
| 2014/0295406 A1 | 10/2014 | Sundvor et al. | |
| 2015/0011020 A1* | 1/2015 | Sundvor | G01N 33/521 436/501 |

* cited by examiner

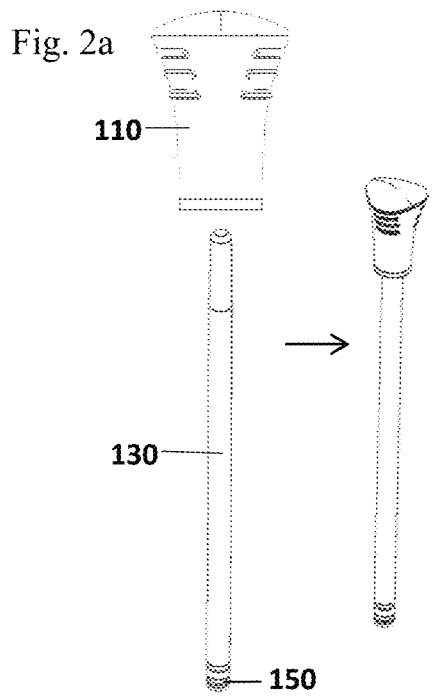
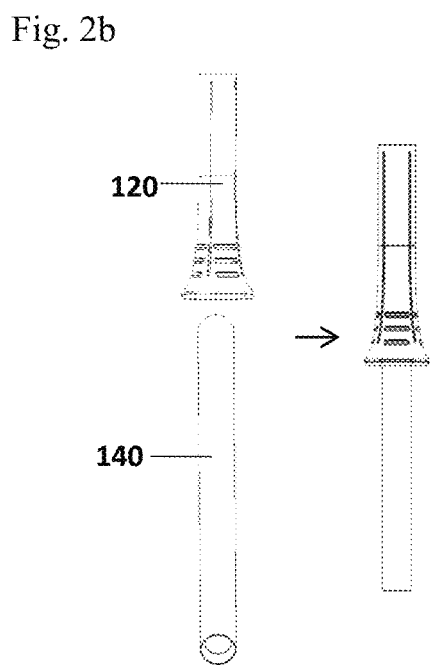
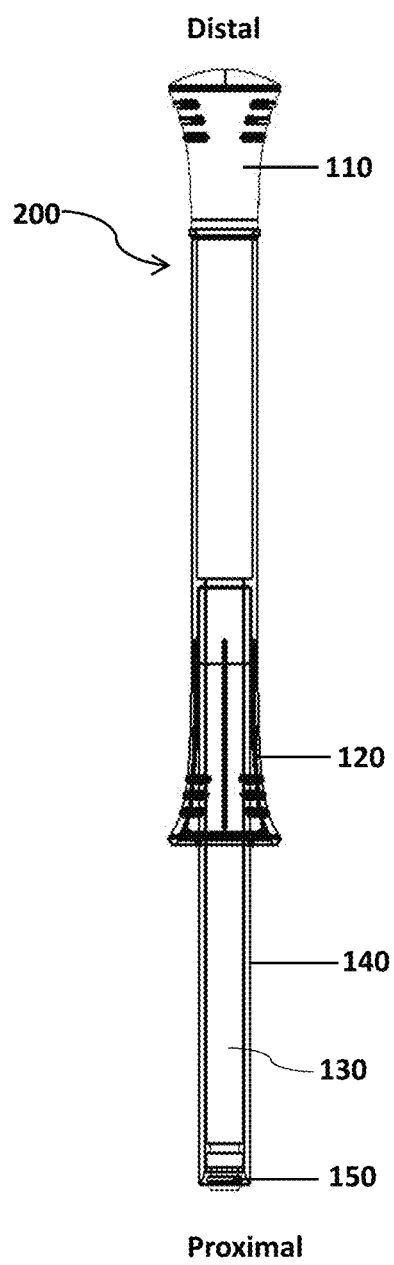

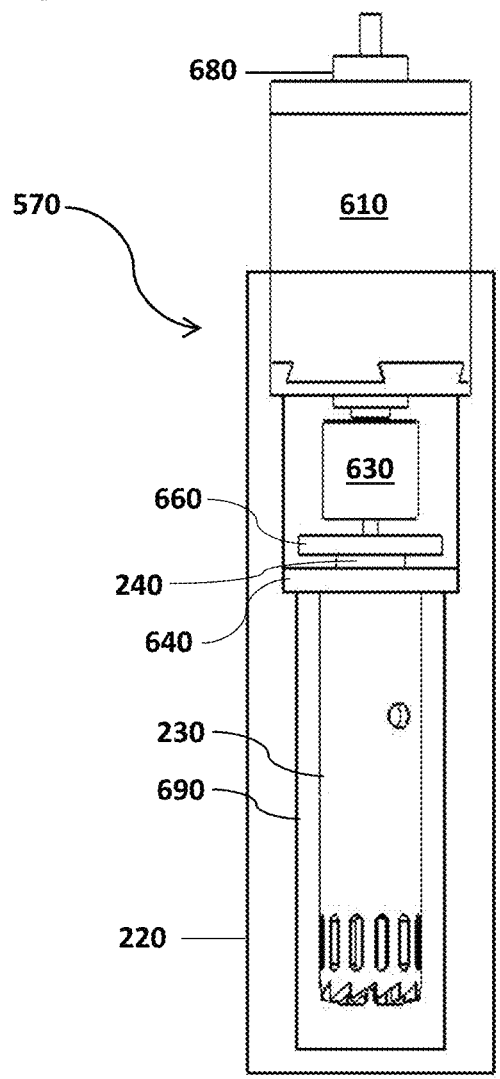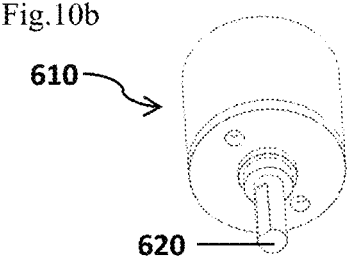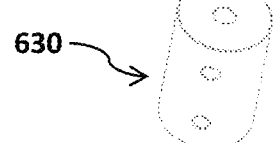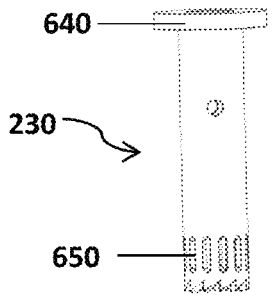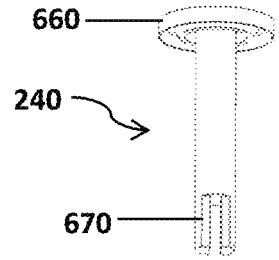

PORTABLE ALLERGEN DETECTION SYSTEM

REFERENCE TO RELATED APPLICATIONS

This application is a 35 U.S.C. 071 U.S. National Stage Entry of International Application No. PCT/US2016/022441 filed on Mar. 15, 2016, which claims priority to U.S. Provisional Application Ser. No. 62/182,900 filed on Jun. 22, 2015, and U.S. Provisional Application Ser. No. 62/133,632 filed on Mar. 16, 2015; the contents of each of which are incorporated herein by reference in their entirety.

FIELD OF THE INVENTION

The present invention relates to systems, devices, and methods for detecting the presence and/or absence of one or more allergens in a sample such as a food sample.

BACKGROUND OF THE INVENTION

Allergy (e.g., food allergy) is a common medical condition. It has been estimated that in the United States, up to 2 percent of adults and up to 8 percent of children, particularly those under three years of age, suffer from food allergies (about 15 million people), and this prevalence is believed to be increasing. During an allergic reaction, the immune system mistakenly targets an allergen as a threat and attacks it. The allergic reaction may affect the skin, the digestive system, the gastrointestinal tract, the respiratory system, the circulatory system and the cardiovascular system; in some allergic reactions, multiple organ systems are affected. Allergic reactions range from mild to severe or life-threatening. Severe symptoms may include difficulty in breathing, low blood pressure, chest pain, loss of consciousness, and anaphylaxis. People having allergies currently manage their allergies by avoiding any food that might contain that specific allergen. These restrictions have a major impact on the patients' quality of life and there remains no method for assessing the true allergen content of food. In the United States, food allergy symptoms send someone to the emergency room every three minutes. A rapid method for determining the presence of an allergen would be of great benefit. A portable device that enables the patients to test their food and determine accurately and immediately the allergen content will be beneficial to provide for an informed decision on whether to consume or not.

Researchers have tried to develop suitable devices and methods to meet this need. U.S. Pat. No. 5,824,554 to McKay teaches a dining mat formed of an absorbent material and small spots of chemical reagents applied to isolated zones on the mat, for detection of food allergens. If the food product contains the allergenic substance, the chemical reagent will change its appearance indicating the presence of the allergenic substance in the food product. The detection limit and the detection specificity are limited by the chemical reagent used in the spots. A drawback is that false negatives are highly possible when analyzing solid food products because of the long reaction times between the solid food products and the spot reagent.

US Patent Application Pub. No. 2008/0182339 and U.S. Pat. No. 8,617,903 to Jung et al. teach a method of detecting an allergen by processing samples with microfluidic chips configured for analysis of one or more allergen indicators, detecting the allergen indicators with one or more detection units, and displaying results with one or more display units. The detecting system comprises a microfluidic chip, a reagent delivery unit, a centrifugation unit, an analysis unit, a detection unit, a display unit, and a recording unit. However, the device is not sufficiently compact to be portable.

US Patent Application Pub. No. 2010/0210033 to Scott et al. teaches a portable device for detecting food allergens comprising a housing, a sample inlet port, a means for indicating the presence of the potential allergen in the sample, and an allergen detection chip comprising an antibody to the potential allergen, wherein the antibody is labeled with a detectable tag. Similarly, false negative results may occur without further processing the sample of the interest such as hard food products.

U.S. Pat. No. 7,527,765 to Royds teaches a food testing device for identifying the presence of harmful contaminants (including allergens) in a food sample, comprising a disposable sample container, a mechanical liquefier including a blade assembly, a test supply compartment with a reagent having an affinity for the harmful contaminant and capable of detecting the harmful contaminant in the liquefied food sample, and producing a visual cue upon recognition of the harmful contaminant.

To implement a rapid, accurate and real-time testing of a food sample, a specific sensor that can rapidly detect allergens is crucial to the testing result. Aptamers, as well as systems, devices, kits and methods of using them in the detection of proteins in food, are disclosed in several patents and patent applications (each of which is incorporated herein by reference in its entirety), including: U.S. Pat. No. 8,633,140 to Kim, et al., which teaches a microarray of functionalized polydiacetylene molecular sensors; U.S. Pat. No. 8,618,046 to Brunner, et al., which teaches a method for treating atherosclerosis using aptamer-based anti-CETP-antibody-inducing antigens; and U.S. Pat. No. 8,614,466 to Rasooly, et al., which teaches a method and system employing a physical principle called "electrical percolation," (flow of electricity through a random resistive network) for electrically detecting biomolecular binding in a semiconductor. In one embodiment, capture molecules for binding target molecules can be an aptamer. U.S. Pat. No. 8,563,298 to Lowery, Jr., et al. teaches NMR systems and methods for the collection and detection of analytes. U.S. Pat. No. 8,507,458 to Yokota, et al. teaches a system for delivering nucleic acids for suppressing target gene expression by utilizing endogenous chylomicron, wherein the nucleic acid may be an aptamer. U.S. Pat. No. 8,236,933 to Herzog, et al. teaches transgenic animals having a reduced level of expression of peptide YY (PYY) and methods of using the transgenic animals for screening a library of aptamers and identifying agonists and antagonists of PYY. U.S. Pat. No. 8,232,584 to Lieber, et al. teaches a fluorescence based nanoscale wire biosensor devices and methods for detecting analytes, wherein an aptamer may be indirectly immobilized relative to the nanoscale wire. U.S. Pat. No. 7,977,462 to Hornbeck et al. teaches lateral flow devices for detecting and quantitating novel tyrosine phosphorylation sites identified in carcinoma and/or leukemia. U.S. Pat. No. 7,973,079 to Mata, et al. teaches biosensors for detecting macromolecules and other analytes that can modulate the activity or availability of serum retinol, retinol-binding protein (RBP) and/or transthyretin (TTR). U.S. Pat. No. 7,855,057 to Gordon, et al. teaches methods, reagents and apparatus for detecting small quantities of protein isoforms (e.g., due to alternative splicing, or different disease protein isoforms or degradation products) in a sample, including using combinations of capture agents, wherein the capture agent may be an aptamer. U.S. Pat. No. 7,850,964 to Vukicevic, et al. teaches nucleic acid biosensors of bone morphogenetic proteins (BMPs), e.g., BMP-1 procollagen c-proteinase, for diagnosis and treatment of bone and soft tissue defects and disorders. Other disclosures of use of aptamers in protein detection include in PCT Publications WO 2009/019007, WO 2009/040113, WO 2010/108657 and WO 2013/104540 to Buchner, et al.

The present inventors have designed and developed reagents (e.g., aptamers) for detecting common food allergens such as peanut, milk, egg, wheat, fish and shellfish. The sequences of certain aptamers are disclosed in commonly owned U.S. Provisional Application Ser. No. 62/026,361, filed on Jul. 18, 2014; U.S. Provisional Application Ser. No. 62/009,958, filed on Jun. 10, 2014; U.S. Provisional Application Ser. No. 61/991,068, filed on May 9, 2014; U.S. Provisional Application Ser. No. 61/938,528, filed on Feb. 11, 2014; U.S. Provisional Application Ser. No. 61/896,399, filed on Oct. 28, 2013; and PCT Application Serial No. PCT/US2014/062656, filed on Oct. 28, 2014; the content of each of which is herein incorporated by reference in their entirety.

Another challenge in developing a rapid and real-time detection testing is to process and extract allergen proteins efficiently from a test sample. The time of processing a sample and the amount of proteins extracted from the sample may significantly affect a detection readout. As discussed herein, the inventors of the present invention developed a portable and reusable device, including a separate sampler and disposable vessels, for fast and accurate detection of the presence and/or absence of one or more allergens in a sample using aptamer-based signal polynucleotides (SPNs). The detection system and device of the present invention can detect much lower amount of allergen presented in a test sample, and complete a detection testing in less than 5 minutes.

SUMMARY OF THE INVENTION

The present invention provides systems, devices and methods for use in allergen detection in various types of samples, in particular, food samples.

One aspect of the present invention is an allergen detection system for detecting the presence and/or absence of one or more allergens in a sample, the system comprising: (a) means for picking-up and/or collecting a test sample; (b) one or more disposables for receiving and processing the test sample, and analyzing the reaction between the allergen(s) being tested and the detection molecules; and (c) a detection device for detecting one or more allergens in the test sample.

In some embodiments, a means for picking up and collecting a test sample may be provided with a means for weighing which ensures a certain amount of the test sample being picked up. In some aspects, the means for picking up and collecting a test sample may be a food pickup corer which is configured for measuring a sized portion of a food sample and/or pre-processing the collected food sample. The corer may have a distal portion provided with a corer top cap at the distal end and a proximal portion provided with a collecting tube, a grip for handling the corer which is connected to the collecting tube, and a plunger inside the collecting tube which has a distal end connected to the top cap and a proximal plunger tip which may protrude from the collecting tube for picking up a food sample. As a non-limiting example, the food pickup corer may further include a spring to indicate the amount of the food sample being picked up.

In embodiments, the disposable may be a disposable test cup or cup-like container which is designed for different allergens. The disposable cup or cup-like container may be designed as an analytical chamber in which a test sample is processed and a reaction between an allergen of interest and the detection molecules and the total protein measurement occur. In some aspects, the test cup or cup-like container comprises a cup body and a cup lid assembly. The cup lid assembly has several ports for a sample pickup (e.g., the food corer), a homogenizer assembly and a means for the flow of the processed test sample solution; and two reaction chambers, one control chamber for measuring the total protein molecules in the test sample in which chemicals for determining the total proteins are present and one analytical chamber for the allergen detection in which the detection molecules (e.g., the signal polynucleotides) specific to an allergen of interest are present. In some aspects, the reaction chambers may be configured to contain a volume of about 10 µL to about 200 µL. The cup body may include a volume of an extraction buffer solution for processing the sample.

In some embodiments of the present invention, the detection device is configured for processing a test sample, extracting allergen proteins from the sample, and detecting the absence, presence and/or the amount of one or more allergens in the test sample. The detection device comprises (a) an external housing that provides support for the components of the detection device; (b) a first part that can be opened for inserting a disposable (e.g., a disposable test cup or cup-like container) when implementing an allergen detection testing; (c) an optional tether for carrying the detection device and an optional plug for power supply.

In accordance with the present invention, the first part of the detection device may be a drawer assembly which can be pulled out from and slide back into the housing. The drawer assembly may be configured to have a well/port for holding a disposable test cup or cup-like container when implementing an allergen detection testing. In other aspects, the first part may be a door that can be lifted and open the well/port for insertion of the test cup or cup-like container.

In accordance with the present invention, the components of the detection device that are integrated for performing an allergen detection testing includes (i) a homogenizer configured for homogenizing a test sample, dissociating and extracting allergen proteins from the test sample in an extraction buffer; (ii) means for driving and controlling the homogenization; (iii) means for driving and controlling the flow of the processed sample solution into the analytical chamber in the cup lid assembly wherein the allergen detection reaction occurs, and the control chamber in the cup lid assembly wherein the total proteins are determined, during the process of the allergen detection testing; (iv) an optical assembly for providing fluorescence excitation and for filtering of fluorescence emission; and for protein absorbance; (v) means for detecting fluorescence emissions from the detection reaction between the allergen in the test sample and the detection molecules in the analytical chamber, and for measuring protein absorbance of chemicals in the control chamber; and means for digitizing detected signals; and/or comparing analog signals directly to thresholds; (vi) a display window for receiving the detected signals and indicating the presence, absence, and/or amount of the allergen in the test sample; and (vii) a power supply.

In some embodiments, the homogenizer of the present detection system is optimized for low power and high speed homogenization of the test sample. In one aspect, the homogenizer comprises a rotor having blades at the proximal end thereof, inside a stator which has one or more slots on the axis of the proximal end thereof. The homogenizer rotor and stator are connected to a motor which can drive and control the movement of the rotor and stator for homogenizing the test sample.

In some embodiments, the processed sample solution is flowed into the analytical chamber and the control chamber in the lid of the test cup through the same path in parallel. The two reactions (i.e., the allergen detection and total protein absorbance) occur simultaneously.

In some embodiments, a pump or an external pressure for driving the liquid flow and controlling the flow rate may be included in the detection device. The pump may be a gas or air pump, or an equivalent thereof.

In some embodiments, the optical detector may be a spectrometer such as an ultraviolet-visible spectrometer and a fluorescent spectrometer, or a camera.

In some embodiments, a printed circuit board (PCB) is connected directly or indirectly to the analytical chamber and the optical assembly for displaying the testing readout. The result may be displayed as numbers, icons, colors and/or letters, or other equivalents.

In some embodiments, the power supply of the present detection device may be a rechargeable or replaceable battery. In other embodiments, the detection device may include a docking station and/or USB charger. In further embodiments, the detection device may be configured to be directly connected to a power supply such as AC/DC converter.

Another aspect of the present invention relates to an allergen detection testing assay for detection of the presence and/or absence of one or more allergens in a sample comprising the steps of (a) obtaining a sample suspected of containing one or more allergens of interest, (b) processing and digesting the obtained sample in an extraction buffer, and dissociating and extracting allergen proteins from the processed sample, (c) mixing the extracted allergen proteins with detection molecules specific to the allergen(s) of interest, (d) treating the mixture with a fluorescent excitation means, and (e) digitizing the detected signals and visualizing the interaction of the detection molecule and the allergen of interest. The detection molecules may be any reagents that can bind to specific allergens, for example, aptamers. The extraction buffer may be optimized for extracting allergen proteins efficiently.

In some embodiments, the present detection assay further comprises a step of instantly determining the total proteins in the test sample, the step comprising mixing the processed sample solution with chemicals that are used for detecting the total proteins in the control chamber in the lid of the test cup (e.g., Pyrogallol Red-Molybate, PRM) and measuring the absorbance at 600 nm intermediately. In some aspects, the allergen detection reaction and the total protein measurement occur in parallel and the signals from the two independent reactions are analyzed simultaneously.

In some embodiments, the signal may be an analog signal. In some aspects, the detection assay may include a signal analysis algorithm that is used to subtract the background and compare to a known threshold determined by standard binding curves.

In some embodiments, the detection system may comprise a user interface that may be accessed and controlled by a software application. The software may run by a software application on a personal device such as a smartphone, a tablet computer, a personal computer, a laptop computer, a smartwatch and/or other device. In some cases, the software may be run by an internet browser. In some embodiments, the software may be connected to a remote and localized server referred to as the cloud.

Other features and embodiments of the present invention will be apparent from the description that follows.

BRIEF DESCRIPTION OF THE DRAWINGS

The foregoing and other objects, features and advantages will be apparent from the following description of particular embodiments of the invention, as illustrated with the reference to the accompanying drawings. The accompany figures are merely for purpose of illustrating exemplary embodiments of the present invention and are not intended to limit the scope of the invention to the exemplary embodiments. Similar reference numerals among the drawings are employed to denote the identical or similar elements presented in different drawings.

FIG. 1 is a detection system in accordance with the present invention.

FIG. 2 illustrates a food corer 200 as an example of sampling mechanism. FIG. 2a and FIG. 2b illustrate the part of the food corer 200. FIG. 2c is an assembled food corer 200.

FIG. 3 illustrates a disposable test cup 300. FIG. 3b illustrates the label/final fluid seal 211. FIG. 3c illustrates the optical window/fluid seal 216. FIG. 3d illustrates the homogenizer rotor 240. FIG. 3e illustrates the cup lid assembly 210. FIG. 3f illustrates the flow tube 221 and the cup flow tube cap and filter assembly 224. FIG. 3g illustrates the cup body 220.

FIG. 4 illustrates alternative designs of the cup lid assembly 210.

FIG. 5 illustrates other embodiments of the filter assembly.

FIG. 6 illustrates an alternative embodiment of reaction chambers 223 within the test cup 200.

FIG. 7 illustrates the external parts of the detection device 100.

FIG. 9 illustrates an assembly of the detection device 100.

FIG. 10 is a homogenizer assembly 570. FIG. 10a illustrates an assembled breadboard homogenizer assembly 570 and its components. FIGS. 10b-10e illustrate a gearhead 610, a coupling 630, a homogenizer stator 230 and a homogenizer rotor 240.

FIG. 12 illustrates a gear train/drive platen 530 connected to a pump 540.

DETAILED DESCRIPTION OF THE INVENTION

Figure 1A:
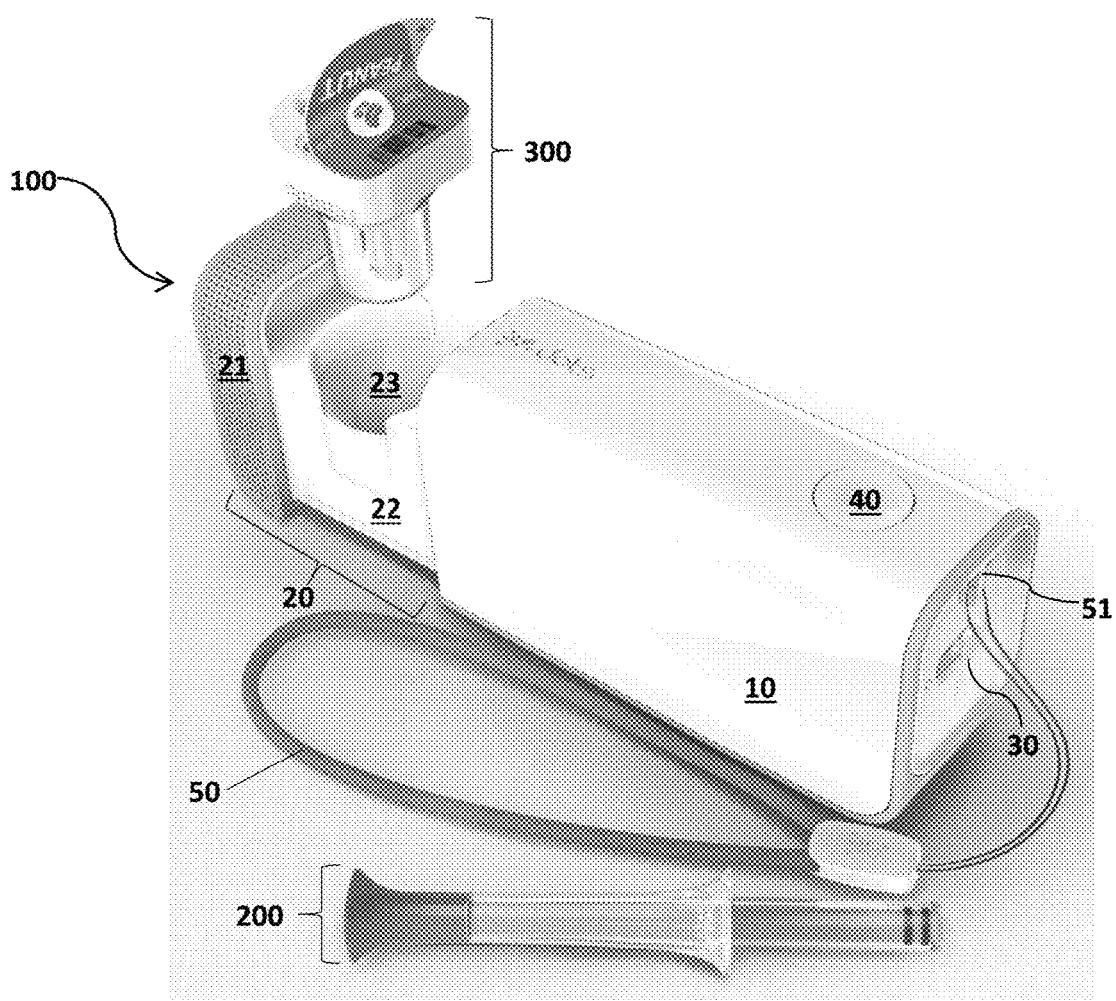
FIG. 1a illustrates a detection system of the present invention comprising a detection device 100, a separate food corer 200 as an example of a means for sampling, an optional tether 50, and a disposable test cup 300.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

The use of analytical devices to ensure food safety has not yet advanced to the point of fulfilling its promise. In particular, portable devices based on simple, yet accurate, sensitive and rapid detection schemes have not yet been developed for detection of the wide variety of known allergens. One of the more recent reviews of aptamer-based analysis in context of food safety control indicated that while a great variety of commercial analytical tools have been developed for allergen detection, most of them rely on immunoassays. It was further indicated that the selection of aptamers for this group of ingredients is emerging (Amaya-González et al., *Sensors,* 2013, 13, 16292-16311, the content of which is incorporated herein by reference in its entirety).

Described herein are systems, devices and methods for detection of allergens, in particular food allergens, using aptamer based signal polynucleotides as detection molecules. As used herein, the term "allergen" means a compound, substance or composition that causes, elicits or triggers an immune reaction in a subject. Allergens may also be referred to as antigens.

One aspect of the present invention is a detection system and device that can specifically detect low concentrations of allergens in a variety of food samples. The detection level of the present systems, devices and methods may be at or below the standard clinical threshold (e.g., one order, two orders, or three orders of magnitude).

In one embodiment, the detection system and/or device of the present invention is a portable product, which is intended to have a compact size which enhances its portability and discreet operation. A user can carry the detection system and device of the present invention and implement a rapid and real-time testing of the presence and/or absence of one or more allergens in a food sample, prior to consuming the food. The detection system and device, in accordance with the present invention, can be used by a user at any location, such as at home or in a restaurant.

In one embodiment of the present invention, the detection system and/or device displays the testing result as a standard readout and the detection can be implemented by any user following the simple instructions on how to operate the detection system and device.

In some embodiments, the detection system and device is designed for simple, fast, and sensitive one-step execution. The allergen detection may be completed in less than 5 minutes, or less than 4 minutes, or less than 3 minutes, or less than 2 minutes, or less than 1 minute. In some aspects, the allergen detection may be completed in approximate 60 seconds, 55 seconds, 50 seconds, 45 seconds, 40 seconds, 35 seconds, 30 seconds, 25 seconds, 20 seconds, or 15 seconds.

In accordance with the present invention, the detection system and device may involve a mechatronic design process integrating electrical engineering, mechanical engineering and computing engineering to implement and control the process of an allergen detection testing, including rechargeable or replaceable batteries, motor drivers for processing the test sample, pumps or actuators for controlling the flow of the processed sample solution to different components of the detection device, and connectors that couple and integrate different components for a fast allergen testing. The detection device of the present invention also includes an optical system which is configured for detection of the presence and concentration of an allergen of interest in a test sample and converts detection signals into readable signals; and a mechanical part which provides support for other parts of the detection device and integrates different parts together as a functional product.

In some embodiments, the detection system and/or device is designed such that the disposables (e.g., a disposable test cup or cup-like container), unique to one or more specific allergens, are designed for receiving and processing a test sample, and assaying the detection test, in which all the solutions are packed. Therefore, all the solutions may be confined in the disposable cup or cup-like container. As a non-limiting example, a disposable gluten test cup may be used to detect gluten in any food sample by a user and discarded after the testing. Accordingly, the detection device may be a dry device and the solutions are packed as disposables. Such a design will avoid cross-contaminations from different allergen tests.

In some embodiments, a separate sample pickup that can measure and size a test sample is provided. In one aspect, the sample pickup can further pre-process the test sample, such as cutting the sample into small pieces, blending, abrading and/or grinding, to make the sample suitable for allergen protein extraction.

Systems and Devices for Allergen Detection

Figure 1B:
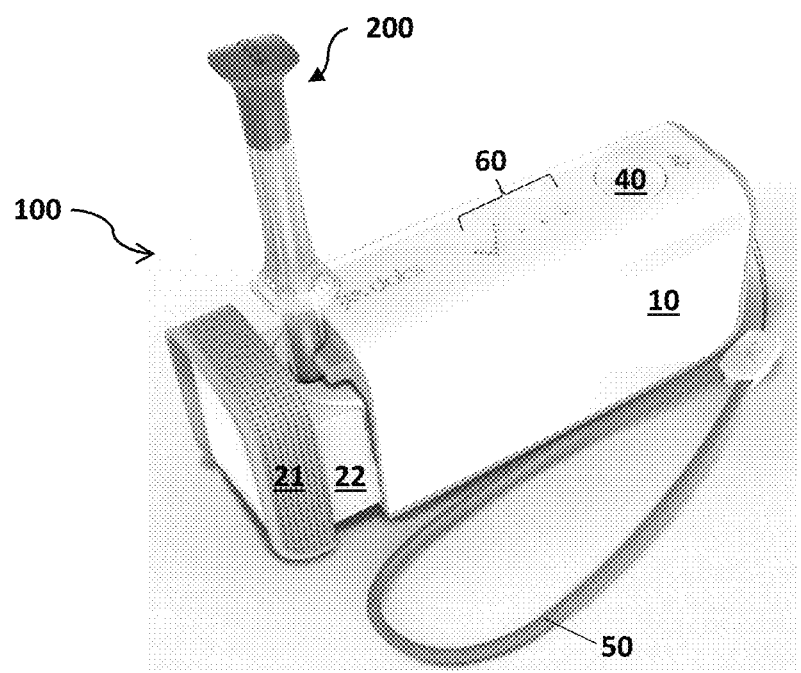
FIG. 1b illustrates an assembly of the detection system of the present invention during the process of implementing an allergen detection testing.

As shown in FIG. 1 (FIG. 1a&FIG. 1b), the detection system of the present invention comprises a detection device 100 configured for processing a test sample and implementing an allergen detection reaction, a sample pickup (e.g., a food corer 200), an optional tether 50 for carrying the detection device 100, and a disposable test cup 300. As used herein, the disposable test cup 300 may be a cup or a cup-like container. The detection device 100 includes an external housing 10 that provides support to the components (as shown in FIGS. 9-16) of the detection device 100, and a drawer assembly 20 which includes a drawer frame 22 and a drawer well 23 for holding a disposable test cup 300. On the front of the drawer frame 22, a drawer grip 21 may be added for a user to operate the drawer assembly in and out of the housing 10. The external housing 10 also provides surface space for buttons that a user can operate the device. An execution/action button 40 that allows a user to execute an allergen detection testing and an on/off slider 30 that allows a user to turn on and/or off the detection device 100 may be included. A display window 60 (FIG. 1b) and an optional plug (not shown) for external power charge may also be included. Optionally, a lanyard 51 for the attachment of the optional tether 50 may be included on the outer surface of the external housing 10.

During the process of implementing an allergen detection test, the food corer 200 with a sample being picked up is inserted into the disposable test cup 300 and the disposable test cup 300 is inserted into the drawer well 23 of the detection device 100 for detection, as shown in FIG. 1b.

The assembly of the detection system shown in FIG. 1 is not intended to be limiting. Other ways to assemble the disposable test cup 300, the food corer 200 and the detection device 100 are within the scope of the present invention. One example includes that the detection device 100 may be configured to grab the disposable test cup 300 from the side or the top of the test cup, such as an alternative assembly shown in FIG. 8. In another aspect, the detection device 100 may be configured to have a door that can be lifted for connecting the detection device 100 with the disposable test cup 300 and the food corer 200.

Collecting a right-sized sample is an important step for implementing allergen detection testing. In some embodiments of the present invention, a means for picking up and collecting test samples (e.g. food samples) is provided. In one aspect, a coring-packer-plunger concept for picking up and collecting a food sample is disclosed herein. Such mechanism may measure and collect one or several sized portions of the test sample and provide pre-processing steps such as cutting, grinding, abrading and/or blending, for facilitating the homogenization and extraction or release of allergen proteins from the test sample. According to the present invention, a separate food corer 200 is designed for picking up different types of food samples and collecting a sized portion of a test sample.

As shown in FIG. 2, the food corer 200 has a distal portion provided with a corer top cap 110 (FIG. 2a) at the distal end, a proximal portion provided with a sample collecting tube 140 (FIG. 2b), a grip 120 for handling the food corer 200 which is connected to the collecting tube 140, and a plunger 130 inside the sample collecting tube 140 which has a distal end connected to the top cap 110 and a proximal plunger tip 150 which may protrude from the sample collecting tube 140 for directly contacting a test sample and picking up a sized portion of the test sample (FIGS. 2a-2c). The shape of the proximal plunger tip 150 may be configured for pre-processing the collected sample.

The parts of the food corer 200 may be designed as any shape for easy handling such as triangular, square, octagonal, circular, oval, and the like.

In other embodiments, the food corer 200 may be further provided with a means for weighing a test sample being picked up, such as a spring, a scale or the equivalent thereof. As a non-limiting example, the food corer 200 may be provided with a weigh tension module. In other embodiments, the food corer 200 may further be provided a feature at the proximal end of the corer which can secure the food corer 200 when it is inserted to the disposable test cup 300 and reduce the spillage of the collected test sample.

Alternatively, other sample pickups may be designed for picking up and collecting different types of test samples. Other designs for sample pickups may include bisecting corer, syringe corer with a blade (e.g., X-Acto blade) across the diameter of the syringe; or alternatively, a syringe corer which is placed directly on top of X-acto blade. The blade may help to divide the cored sample into two or more small pieces, making them easier to be processed and homogenized.

The food corer 200 and the plunger 130 may be made of plastic materials, including, but not limited to polycarbonate (PC), polystyrene (PS), polymethylmethacrylate (PMMA), polyester (PET), polypropylene (PP), high density polyethylene (HDPE), polyvinylchloride (PVC), thermoplastic elastomer (TPE), thermoplastic urethane (TPU), acetal (POM), polytetrafluoroethylene (PTFE), or any polymer, and combinations thereof. The plunger 130 may be sealed to the corer using any materials that can provide resistance to heat, liquids and UV light, etc., for example, Buna-n, Fluoroelastomer, Silicone, ethylene propylene diene monoer (EPDM) elastomers, Neoprene, polyurethane (PU), and PTFE.

In accordance with the present invention, the detection system includes one or more disposables which are designed for processing test samples, storing reaction solutions and extracting allergen proteins and wherein the allergen detection reaction occurs and the total proteins are measured. That is, a disposable is intended to be used only once for an allergen testing in a sample and therefore may be made of low cost plastic materials, for example, transparent high density polyethylene (HDPE), polycarbonate (PC), polymethylmethacrylate (PMMA), polypropylene (PP), polyvinylchloride (PVC), polystyrene (PS), polyester (PET), or other thermoplastics. Accordingly, the disposables may be designed for any particular allergen of interest. In some embodiments, these disposables may be designed for one particular allergen only, which may avoid cross contamination with other allergen reactions. In other embodiments, these disposables may be designed for detecting two or more different allergens in a test sample in parallel. In some aspects, the disposables may be designed for detecting two, three, four, five, six, seven, or eight different allergens in parallel.

In some embodiments, the disposables may be a disposable test cup 300 which may be a disposable cup or a cup-like container, as shown in FIG. 3. In accordance with the present invention, a disposable test cup 300 includes a cup lid assembly 210 and a cup body 220 for receiving a test sample, processing the sample and binding the allergen being detected to the detection molecules (e.g., signal polynucleotides (SPNs)), as shown in FIG. 3a. FIG. 3b through FIG. 3g show an exploded view of the disposable test cup 300. FIG. 3b illustrates the label/final fluid seal 211. FIG. 3c illustrates the optical window/fluid seal 216 with test cup port 214. FIG. 3d illustrates the homogenizer rotor 240. FIG. 3e illustrates the cup lid assembly 210. FIG. 3f illustrates the flow tube 221 and a cap and filter assembly 224. FIG. 3g illustrates the cup body 220. The cup lid assembly 210 has multiple functions in addition to the closure of the disposable test cup 300 (FIG. 3a). In one aspect, the cup lid assembly 210 has three ports: a rotor port 212 for housing a homogenizer rotor 240 and a homogenizer stator 230; a food corer port 213 for receiving a food corer 200 and receiving a test sample, and a test cup port 214 for connecting the disposable test cup 300 to a flow controlling component (e.g., vacuum or pressure ducts); a fluid channel 215 for bringing the extracted sample solution to the two reaction chambers 223 (FIGS. 3a-3g). Through the food corer port 213, the test sample collected by a food corer 200 can be plunged into the cup body 220 for homogenization and extraction of allergen proteins from the sample. Through the test cup port 214, which is used to link the disposable test cup 300 to the flow control component(s) of the detection device 100, the extracted allergen proteins from the test sample may be pumped or pressed out of the cup body 220 and flow through the flow tube 221 into the fluid channel 215 and then to the two reaction chambers 223. An optical window/fluid seal 216 provides liquid sealing and optical access to the two reaction chambers 223. A label/final fluid seal 211 provides final liquid seal and identification for the cup assembly (e.g. a designation of gluten that indicates the disposable test cup 300 is used for detecting the gluten allergen). A cap and filter assembly 224 is provided to prevent humidification of the solid reagents stored in the two reaction chambers 223 and filtration of the large particles from the homogenized protein/buffer solution.

Figure 3A:
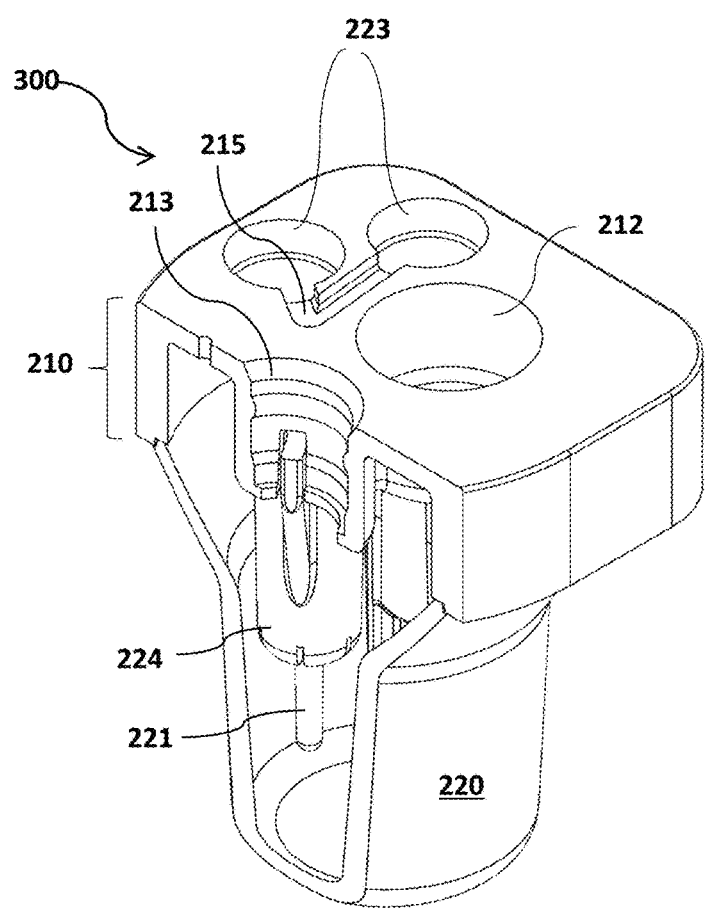
FIG. 3a is an assembled cup having a cup lid assembly 210 and a cup body 220.
Figure 3B:
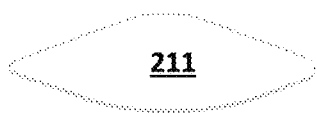
FIGS. 3b through 3g show an exploded view of the disposable test cup 300.
Figure 3C:
Figure 3D:
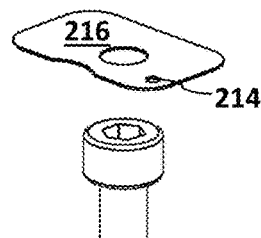
Figure 3E:
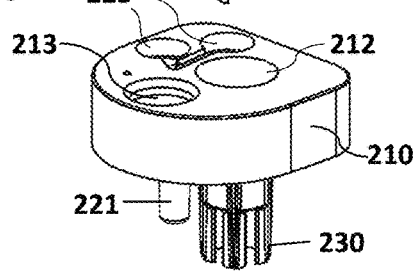
Figure 4A:
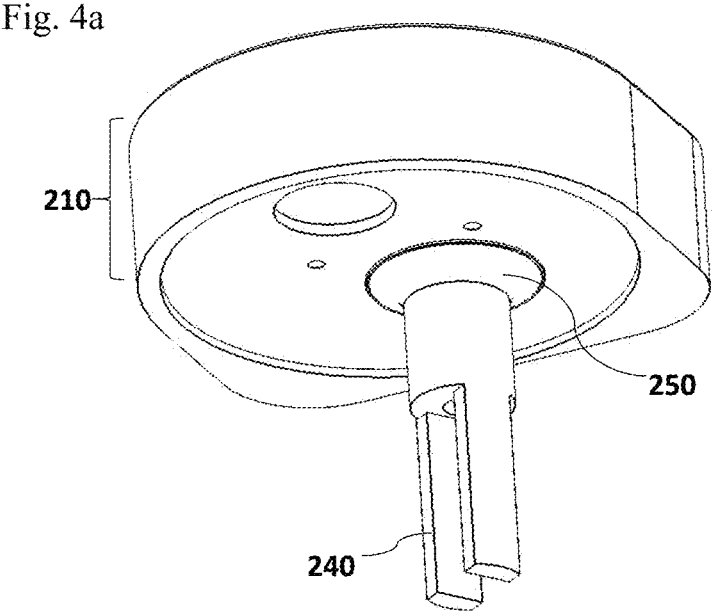
FIG. 4a is an alternative configuration of the homogenizer rotor 240 which is connected to the rotor port 212 through a membrane seal 250, without the homogenizer stator 230.

Alternatively, the homogenizer rotor 240 may be connected to the homogenizer rotor port 212 on the lid assembly 210 as shown in FIG. 4a. In this particular embodiment, the homogenizer stator 230 which is as shown in FIGS. 3a and 3e, welded to the homogenizer rotor port 212 is not necessary required. The homogenizer rotor 240 may be directly linked to the homogenizer rotor port 212 at the inner side of the lid assembly 210, through a membrane seal 250. The seal materials may include, but are not limited to thermoplastic polyurethane (TPU), thermoplastic elastomer (TPE), thermoset materials such as Silicone, Rubber (e.g., Buna-N, Neoprene, and Santoprene). The connected two parts which may be composed of materials with different thermo-plasticity and hardness may be fabricated using two-shot plastic injection molding. The connection between the homogenizer rotor 240 and the rotor port 212 may also be produced using over-molding injection molding, thermally welding, ultrasonically welding and/or gluing process, or any other appropriate molding technologies.

In one embodiment of the present invention, two independent reaction chambers 223 are provided in the cup lid assembly 210, including one analytical chamber for the allergen detection reaction in which the detection molecules (e.g., aptamer derived signaling polynucleotide) specific to an allergen of interest are provided and wherein the allergen detection reaction occurs, and one control chamber for the total protein measurement in which the chemical solution (e.g., pyrogallel red molecules) for determining the total proteins in the test sample are provided. The two reaction chambers 223 on the top of the cup lid assembly 210 are connected to the fluid channel 215 through which the flow of the extracted protein solution is pumped or pressed into the two reaction chambers 223. The detection molecules specific to an allergen and the chemical solution for total protein measurement in the reaction chambers 223 may be dry powder and can be mixed with the processed sample solution that flows from the flow tube 221 and the fluid channel 215 to the two reaction chambers 223. Alternatively, the detection molecules and the chemical solution may be resuspended in an appropriate buffer. The two reaction chambers 223 may be configured to receive the processed sample solution in parallel or sequentially, but preferably in parallel. The fluorescent signals from the allergen analytical chamber and the protein absorbance at certain light wavelength from the control chamber will be detected by an optical system of the detection device 100. In some embodiments, more than one allergen analytical chambers may be configured on the top of the cup lid assembly 210, such as two, or three, or four, for five, or six, or seven or eight allergen analytical chambers, in each of which the detection molecules specific to a different allergen may be provided. Such multiplex design will allow a user to detect several allergens in a test sample at the same time, in condition that the user is allergic to multiple allergens. In some aspects, these reaction chambers are designed for parallel detection reactions. That is to say, all reactions, including the total protein determination, may occur in parallel.

Figure 4B:
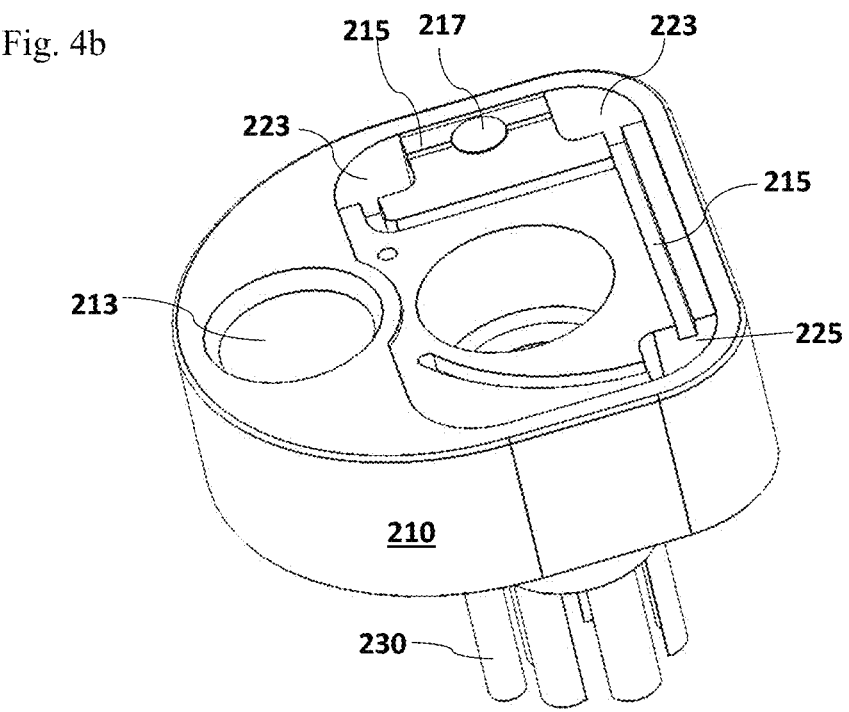
FIG. 4b illustrates an alternative configuration of reaction chambers on the top of the lid assembly 210.

As noted above and shown in FIG. 4b, it is within the scope of the present invention that more than two reaction chambers may be designed on the top of the cup lid assembly 210. In certain embodiments, three or more chambers may be designed on the top of the lid assembly 210. In one particular embodiment, three chambers are provided including two reaction chambers 223 and one additional chamber 225 which may be used to measure non-specific background signals from the allergen detection assay. FIG. 4b illustrates an exemplary configuration of the three chambers on the top of the cup lid assembly 210. It is understandable to one of skill in the art that this particular configuration is illustrated to present the concept thus is not limiting. The position of each chamber may vary dependent on the design of the cup lid assembly 210 and the number indications are not limiting neither. Each chamber may be designated as an analytic chamber for detecting signals from the interaction between an detection molecule and the allergen of interested in the test sample, or a chamber for measuring total proteins isolated from the test sample, or a control chamber for measuring non-specific background signals from the detection assay. The three chambers may be connected to the fluid channel 215, receiving a portion of the processed test sample solution through the flow tube 221 and the fluid channel 215. To avoid the interference among different chambers which may cause misleading detection results, one or more air vent 217 may be added within the fluid channel 215 to prevent the liquid flow between chambers.

Figure 5A:
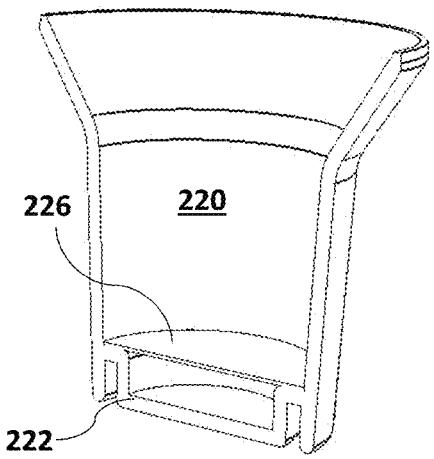
FIG. 5a illustrates that an alternative filter membrane 226 may be provided at the bottom of the cup body 220 with certain distance from the cup base 222.
Figure 5B:
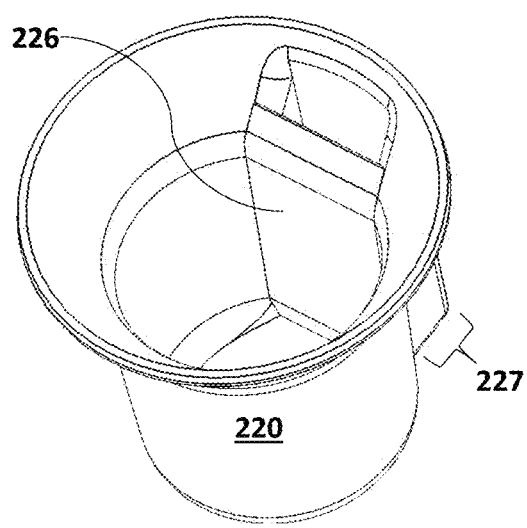
FIG. 5b illustrates another alternative in which the filter membrane 226 is aligned in parallel with the cup wall and a small chamber 227 may be connected to the cup body 220 for receiving the filtered sample solution.

As described in FIG. 3, in certain embodiments, a flow tube cap and filter assembly 224 may be attached to the flow tube 221 for filtering the processed test sample before being delivered to the reaction chambers 223 and the additional control chamber 225. Alternatively, the filtering assembly 224 may be replaced by a simple filter membrane 226. In some aspects, the membrane filter 226 may be aligned in parallel with the cup base 222 of the cup body 220 with a certain distance to the cup base 222 (as shown in FIG. 5a). The room between the filter membrane 226 and the cup base 222 allows holding a filtered sample solution. In other aspects, the filter membrane 226 may be inserted into the cup body 220 in parallel with the wall of the cup body 220 with a certain distance to the wall, allowing enough room for holding the filtered sample solution before being delivered (e.g., by pumping or vacuuming) to the reaction chambers 223 and/or the additional control chamber 225. Alternatively, a small chamber 227 protruding out from the side wall of the cup body 220 where the filter membrane 226 is attached, may be provided; the small chamber 227 will hold the filtered sample solution before being delivered to the reaction chambers 223 and/or the additional control chamber 225 (FIG. 5b). In other aspects, more than one filter membrane 226 may be provided. As a non-limiting example, two filter membranes 226 may be inserted into the cup body 220 (similar to the filter membrane 226 shown in FIG. 5a), one filter membrane with a larger pore size on the top of the space for holding filtered sample solution and the other filter membrane with a smaller pore size underneath the space for further filtering the sample solution.

The filer membrane 226 may be a nylon, PES (polyethersulfone), Porex™, or the membrane polymers such as mixed cellulose esters (MCE), cellulose acetate, PTFE, polycarbonate, or the like. It may be a thin membrane (e.g., 150 µm thick) with high porosity. In some aspects, the pore size of the filter membrane 226 may range from 20 µm to 300 µm, or any size in between. For example, the pore size may be 20 µm, 25 µm, 30 µm, 35 µm, 40 µm, 45 µm, 50 µm, 55 µm, 60 µm, 65 µm, 70 µm, 75 µm, 80 µm, 85 µm, 90 µm 100 µm, 150 µm, 200 µm, 250 µm, or 300 µm.

Figure 6A:
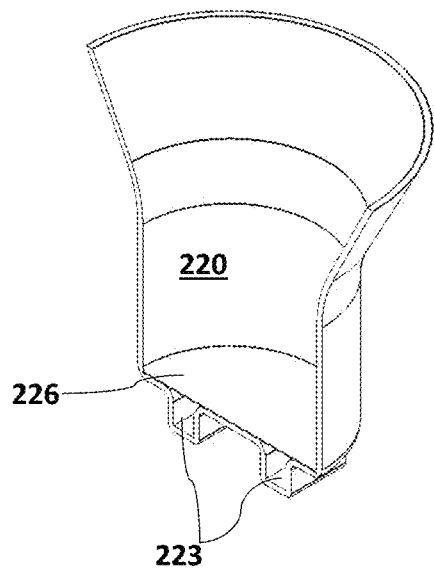
FIG. 6a is a side view of the reaction chambers 223 which are located at the bottom of the cup body 220.
Figure 6B:
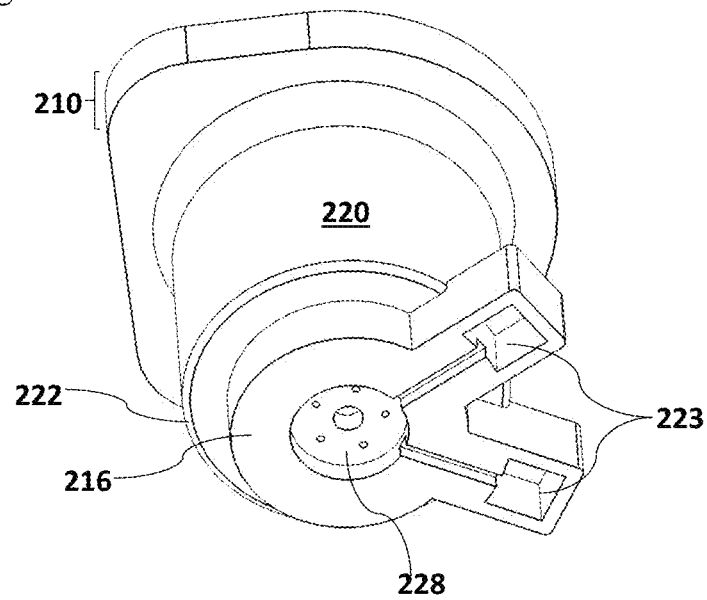
FIG. 6b is a view from the bottom of the test cup 200, demonstrating a valve 228 which is provided to control the fluid flow to reaction chambers 223.

It is within the scope of the present invention that one or more reaction chambers 223 and the optional control chamber 225 are not necessarily being designed on the top of the lid assembly 210. The one or more reaction chambers 223 and the additional control chamber 225 may be located at any parts of the test cup or the cup like container 300. In addition to the configurations illustrated in FIG. 3 and FIG. 4b, alternative embodiments may also be provided. As illustrated in FIGS. 6a and 6b, the one or more reaction chambers 223, and/or the additional control chamber 225 may be located at the bottom of the cup body 220, directly receiving the test sample solution after being filtered by the filter membrane 226. FIG. 6b further illustrates a view from the bottom of the test cup or cup-loke container 300. According to this particular embodiment, the optical window/fluid seal 216 is used to seal the chambers and to provide a window to read the detection signals. Additionally a valve 228 may be provided, allowing control of the flow of the processed sample solution. The valve 228 may be an umbrella valve, a duckbill valve, other one way valves, a frangible seal or the like. For example, internal frangible seals may be used to enable the controlled release of the sample solution.

Similarly, the cup lid assembly 210 may be composed of a thermoplastic including, but not limited to polymethylmethacrylate (PMMA), polystyrene (PS), polycarbonate (PC), polyester (PET), polypropylene (PP), high density polyethylene (HDPE) and polyvinylchloride (PVC), or combinations thereof.

Figure 3F:
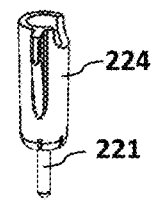
Figure 3G:

The cup body 220 is intended to receive a test sample from the food corer 200 to be homogenized for extraction of allergen proteins and may have a wider distal end which is connected to the cup lid assembly 210, and a cup base 222 (FIG. 3g). In certain embodiments, the cup body 220 contains a volume of extraction buffer for extraction and digestion of the test sample. The volume of extraction buffer may range from about 100 µL to about 500 µL, or from about 500 µL to about 2.5 mL. In the cup the digestion volume should be 500 µL-5 mL. In the detection chambers it should range from 10 µl to 300 µl. In some embodiments, the volume of buffer may be 100 µL, or 200 µL, or 300 µL, or 400 µL, or 500 µL, or 1 mL, or 1.2 mL, or 1.4 mL, or 1.6 mL, or 1.8 mL, or 2.0 mL, or 2.5 mL.

In other embodiments of the present invention, the allergen detection reaction may occur in the cup body 220 and the fluorescent signals will be detected by an optical system of the detection device 100. Accordingly, the cup body 220 may include detection molecules which specifically bind to one or more allergens to be tested. The detection molecules may be confined in any local regions of the cup body 220, such as at the bottom of the cup base 222 and released into the cup body and mixed with the extracted protein solution for the detection assay. The allergen and detection molecule mixture may be pumped or pressed into an analytical chamber included in the reaction chambers 223 for signal analysis. In some aspects, the cup body 220 may be divided into several separate parts, one part configured for receiving and processing the test sample collected by the food corer 200 or other types of samplers and extracting allergen proteins from the test sample, and one part configured for detecting the allergens in the test sample.

Typically, a disposable test cup 300 has a capacity suitable for a sample of about 0.25-5 g. The cup body 220, which is intended for dissociating/homogenizing the test sample in an extraction buffer, may have a capacity of about 0.5 mL-3 mL.

In other embodiments, the cup body 220 may be made of soft materials. In such case, after insertion of a test sample, the cup body 220 including the solution inside may be pressed into the analytical chamber which is one of the reaction chambers 223 on the top of the cup lid assembly 210 by an external pressure, such as a pressure from the detection device 100. Such pressure, compression, or agitation may also serve to process the test sample.

In some embodiments, the cup body 220 and/or the separate parts of the cup body 220 may be in any shape. In this context, the cup lid assembly 210 is configured to match the shape of the cup body.

In some embodiments, the detection device 100 may be configured to have two parts: an external housing that provides support surfaces for the components of the detection device 100; and a part that can open the detection device 100 for inserting an assembly of a disposable test cup 300 and a food corer 200. One embodiment of the allergen detection device 100 according to the present invention is depicted in FIGS. 1 and 4. As illustrated in FIG. 1 (FIG. 1a & FIG. 1b), the detection device 100 comprises an external housing 10 that provides support for holding the components of the detection device 100 together and integrates them as a functional integrity for implementing an allergen detection testing; and a drawer assembly 20 that may be pulled out from and slide back into the external housing 10. The housing 10 may be formed of plastic or other suitable support material.

Figure 7A:
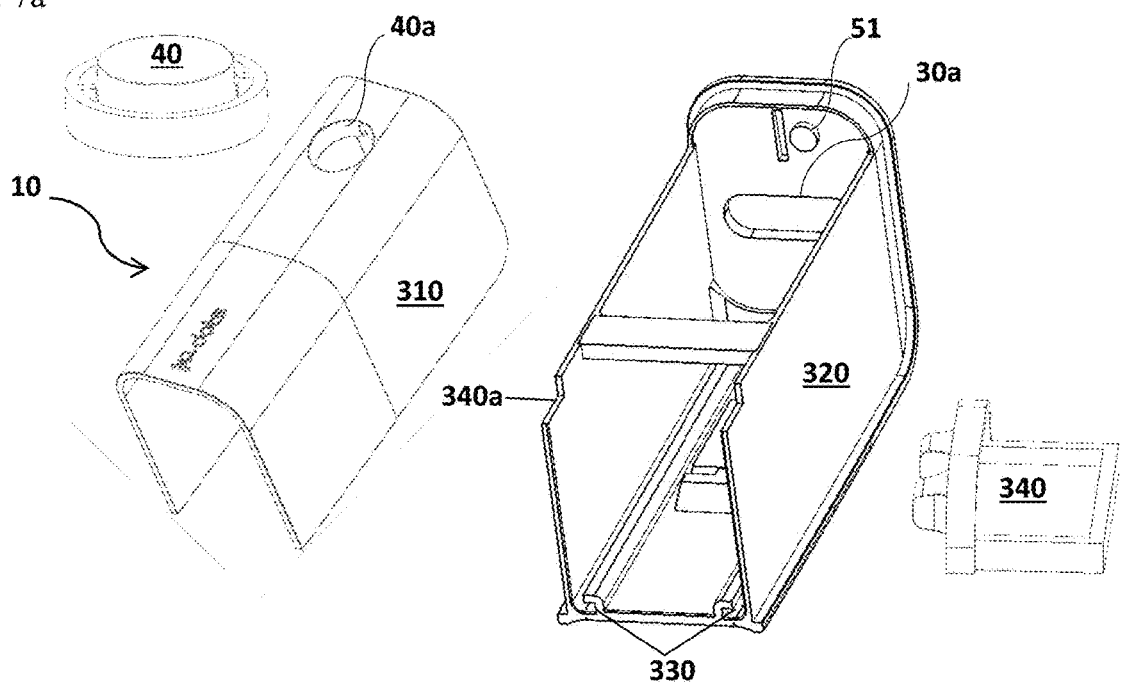
FIG. 7a illustrates the housing 10.
Figure 7B:
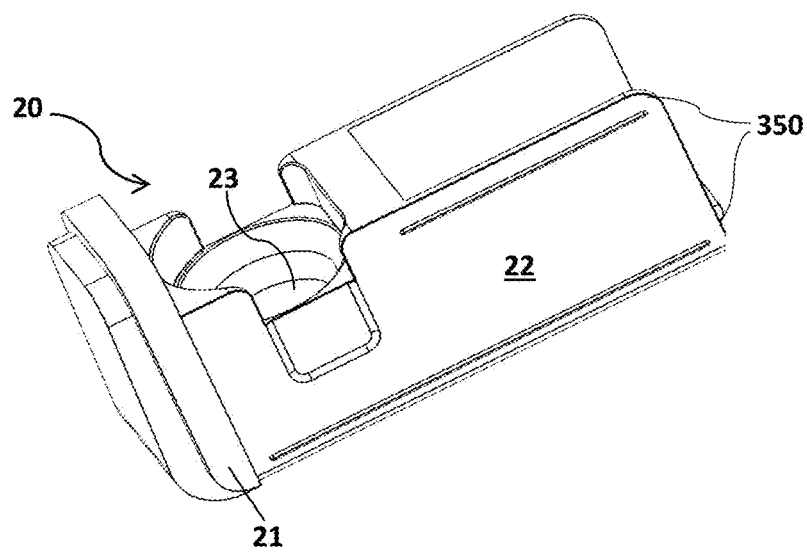
FIG. 7b illustrates the drawer assembly 20.

As shown in FIG. 7a, the external housing 10 may include a housing cover 310 and a housing base 320, on which a button port 40a for the execution/action button 40, and an on/off slider port 30a for the on/off slider 30 are provided. Additionally, an alignment 340 may be incorporated into the alignment site 340a on the top front of the external housing 10 for aligning the disposable test cup 300 with the detection device 100 when implementing an allergen detection test. A groove 330 at each side of the bottom of the housing base 320 is used to sled the drawer assembly 20. The drawer assembly 20 (FIG. 7b) may include a drawer frame 22 on the front of which there is a drawer grip 21 which is configured for a user to handle the drawer assembly 20 during a detection test, and a drawer well 23 for insertion of a disposable test cup 300. A sled (or chimb) 350 at each side of the drawer frame 22 is provided for sliding the drawer assembly 20 along the groove 330 of the housing base 320.

When the detection device 100 is not in use, the drawer assembly 20 is pushed back into the housing 10, so the detection device 100 is closed and may be easily carried with or stored in a bag (e.g., a handbag).

Figure 8:
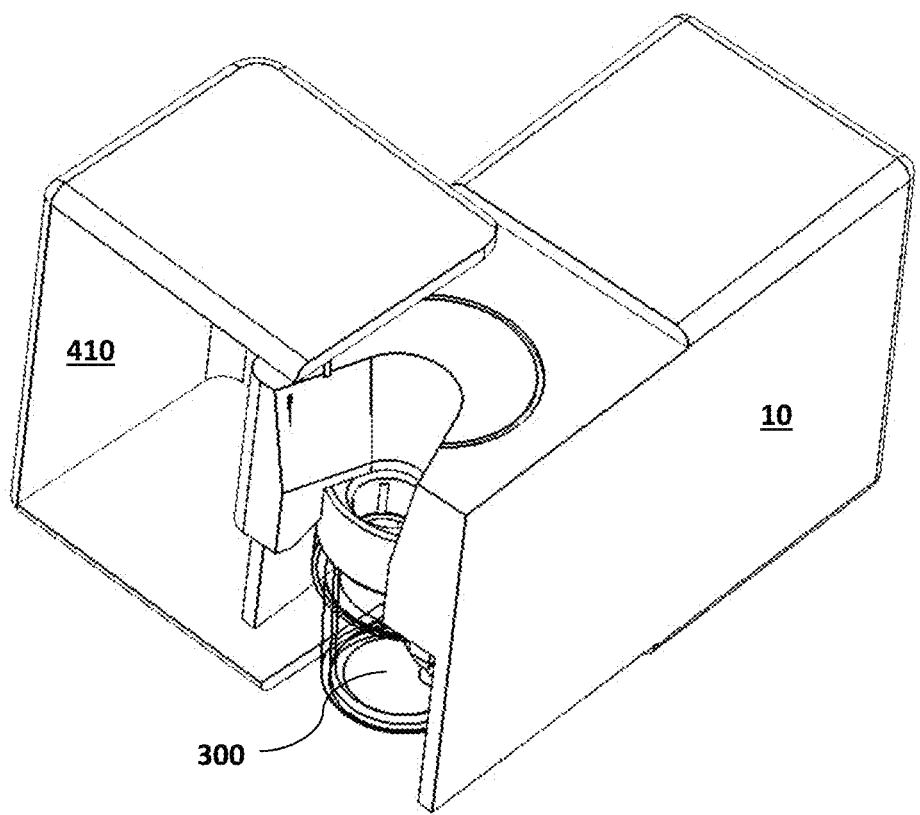
FIG. 8 illustrates an alternative assembly of the detection system of the present invention having a claw-like rotating door 410 or a swinging housing configuration.

Alternatively, other configurations that allow the drawer well 23 for holding a disposable test cup 300 being reachable may be designed in accordance with the present invention. As a non-limiting example, a claw-like rotating door 410 may be connected to the external housing 10 (as illustrated in FIG. 8). The detection device 100 may be placed over the disposable cup 300 with the claw-like rotating door 410 to close over the cup during operation. As another non-limiting example, a hinged door that can be lifted may be designed to open the external housing 10 during an allergen detection testing.

To execute an allergen detection test, the detection device 100 is provided with a homogenizer which is configured for homogenizing a test sample and extracting allergen proteins from the test sample in an extraction buffer; means (e.g., a motor) for operating the homogenizer and necessary connectors that connect the motor to the homogenizer; means for driving and controlling the flow of the processed sample solution during the process of the allergen detection testing; an optical assembly for providing fluorescence excitation and for filtering of fluorescence emission; means for detecting fluorescence emissions from the detection reaction between the allergen in the test sample and the detection molecules, and the protein absorbance from the control chamber; means for digitizing detected signals; a user interface that displays the test results; and a power supply.

Figure 9A:
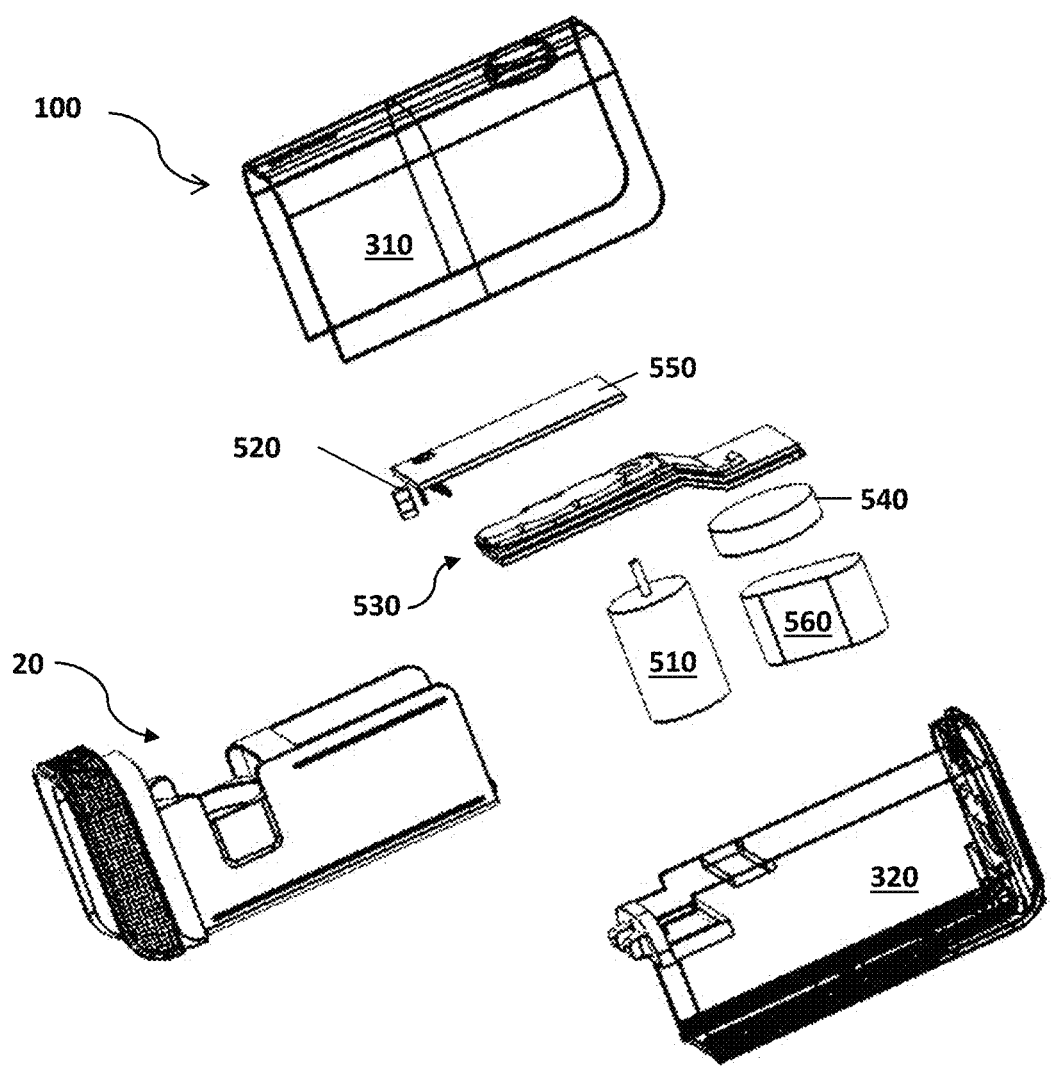
FIG. 9a illustrates the individual components of the detection device 100.
Figure 9B:
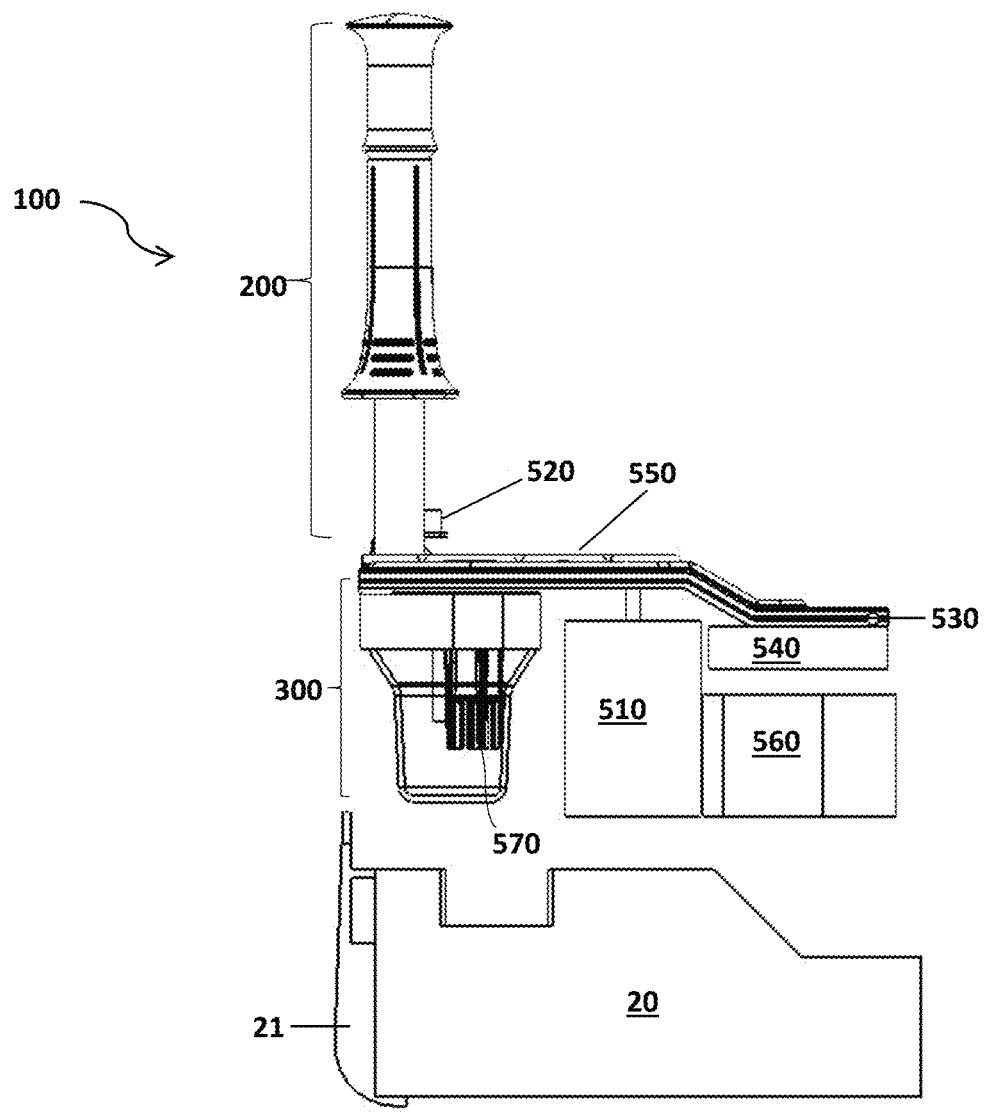
FIG. 9b illustrates the components of the detection device 100 configured inside the external housing 10 (not shown).

In one embodiment of the present invention, as shown in FIGS. 9a and 9b, the components of the detection device 100, include a motor 510 which may be connected to the homogenizer assembly 570 that is assembled inside the cup body 220 (not shown), an optical assembly 520 that is connected to the two reaction chambers 223 (not shown) (i.e., the allergen analytical chamber and the total protein control chamber) on the top of the cup lid assembly 210 (not shown) of the disposable test cup 300, a gear train/drive platen 530 for driving the rotor during homogenization in an allergen detection testing, a pump 540 for controlling and regulating the flow rate, a PCB 550, and a power supply 560. The components are held inside the drawer assembly 20 which may have a drawer grip 21. The detection device is enclosed by a housing cover 310 and a housing base 320. FIG. 9b illustrates a view of the detection device 100 when different components are assembled and integrated as a functional device while FIG. 9b illustrates different components of the detection device 100 with the food corer 200 assembled with the test cup 300.

In accordance with the present invention, a homogenizer is designed small enough to fit into a disposable test cup 300. Additionally, the homogenizer of the detection device 100 may be optimized for increasing the efficacy of sample homogenization and allergen protein extraction.

FIG. 10 illustrates one embodiment of a homogenizer assembly 570 shown in FIG. 9b. FIG. 10a illustrates an assembled breadboard homogenizer assembly 570 which is held inside a cup body 220 and its components. FIGS. 10b-10e illustrate a gearhead 610, a coupling 630, a homogenizer stator 230 and a homogenizer rotor 240. A homogenizer rotor 240 and a homogenizer stator 230 are assembled through the homogenizer rotor port 212 on the top of the cup lid assembly 210 (not shown, see FIG. 3). The homogenizer rotor 240 has a distal end provided with a top rotor cap 660 and a proximal end comprising one or more rotor blades 670 or the equivalent thereof (FIG. 10e). The rotor cap 660 may be connected to the homogenizer rotor port 212 (not shown) and the homogenizer rotor 240 is inserted into the cup lid assembly 210 (not shown) through the homogenizer rotor port 212 (not shown). The homogenizer rotor 240 is configured to rotate inside the homogenizer stator 230 (FIG. 10d) and pull the test sample from the food corer 200 (not shown) into the bottom of the processing chamber 690. The homogenizer stator 230 has a distal end provided with a stator cap 640 and a proximal end comprising one or more small stator slots 650 (FIG. 10d), which extend into the cup body 220. Through the stator cap 640, the homogenizer stator 230 is seated within the homogenizer rotor port 212 of the cup lid assembly 210 (not shown). During processing, the test sample is forced radially out through the stator slots 650 at the proximal end of the homogenizer stator 230. The homogenizer stator 230 acts as a flow breaker to largely prevent rotation of the sample, and to introduce large mechanical energies in very small space. A coupling 630 (FIG. 10c) at the distal portion of the homogenizer links the homogenizer rotor 240 to a gearhead 610 (FIG. 10b), which is a part of a gear train or a drive for connection to a motor 510 (not shown, see FIGS. 9a, 9b, and 11). The gearhead 610 reduces the speed of the motor 510 and increases torque in the liquid and the coupling 630 connects the actuator shaft 620 to the homogenizer rotor 240. The proximal portion of the homogenizer (i.e., the rotor blades 670 and the stator slots 650) spins within the cup body 220 to create shear in the liquid between the stationary teeth of the homogenizer stator 230 and the rotating tines of the homogenizer rotor 240 (FIG. 10a). A shuttle vertical guide pin 680 is positioned on top of the assembly 570 to connect the motor 510 (not shown). The vortex is greatly reduced and more energy is introduced in the shearing gap between the rotor and stator. Particles are reduced in size by hitting sharp edges, shearing between the edges of the rotor blades and stator slots.

In some aspects, a heating system (e.g. resistance heating, or peltier heaters) may be provided to increase the temperature of homogenization, therefore to increase the effectiveness of sample dissociation and shorten the processing time. The temperature may be increased to between 60° C. to 95° C., but below 95° C. Increased temperature may also facilitate the binding between detection molecules and the allergen being detected. Optionally a fan or peltier cooler may be provided to bring the temperature down quickly after implementing the test.

Figure 11:
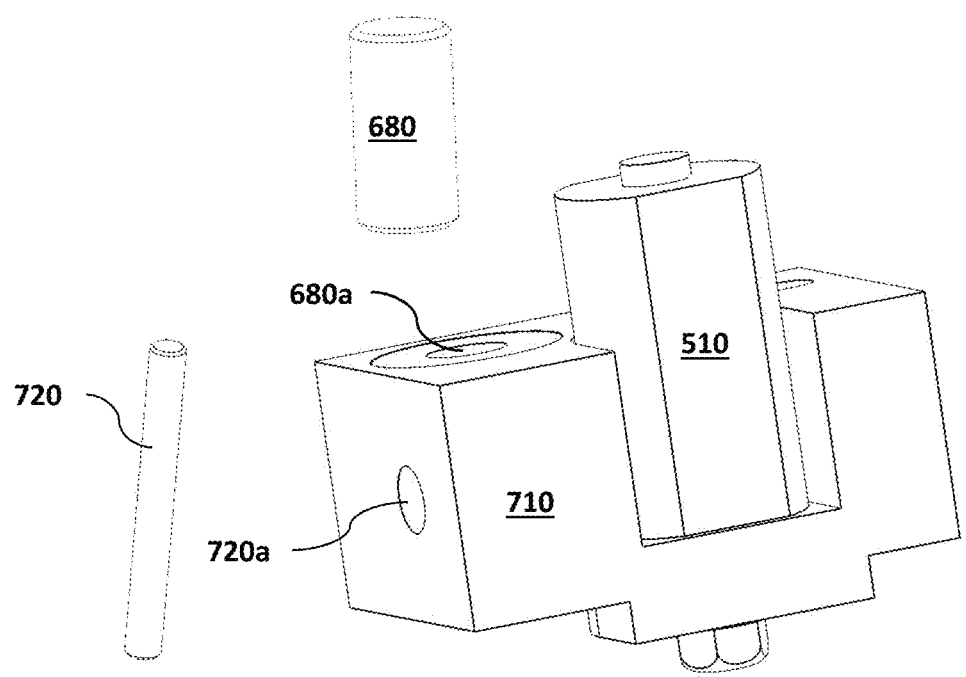
FIG. 11 illustrates a motor shuttle 710 and a motor 510 assembly.

Turning to FIG. 11, in some embodiments of the present invention, a motor 510 may be connected to the homogenizer assembly 570 (not shown) through a motor shuttle 710 for engaging the homogenizer rotor 240 (not shown) and homogenizer stator 230 (not shown). A shuttle vertical guide pin 680 through a pin port 680a on the motor shuttle 710 guides the gearhead 610 and the actuator 620 of the homogenizer assembly 570 to the motor 510. A motor shuttle lift pin 720 can further align and raise/lower the motor shuttle 710 and the motor 510 through a lift pin port 720a.

In the sample processing cup body 220, an extraction buffer preloaded in the cup and a test sample plunged from the food corer 200 are mixed. Driven by the motor 510, the homogenizer assembly 570 will homogenize the test sample in the extraction buffer and dissociate/extract allergen proteins. The processed sample solution may be pumped or pressed through the flow tube 221 to the fluid channel 215 on the top cap of the cup lid assembly 210, then to the analytical chamber which is one of the reaction chambers 223, in which the processed sample solution is mixed with the pre-loaded detection molecules (e.g., SPNs) for the detection testing. In parallel, a portion of the processed sample solution is pumped or pressed to the other control chamber which is one of the reaction chambers 223 on the top of the cup lid assembly 210, in which the extraction solution is mixed with the preloaded total protein indicator molecules (e.g., PRM) for total protein determination.

In some embodiments, the processed test sample may be further filtered through means that can push the processed sample solution through a filter membrane (e.g., a filtering means connected to the homogenizer assembly 570) prior to the flow of the extraction solution to a reaction chamber 223.

One example is a cap and filter assembly 224 illustrated in FIG. 3f. The filter pores can be between 0.2 u to 300 u. The filter can be made from any low binding material including, but not limited to, PES (Polyethersulfone), PCTE (Polycarbonate) or PVDF (polyvinylidene difluoride).

In some embodiments, the coupling 630 may have different sizes at each end of the coupling 630, or the same sizes at each end of the coupling 630.

As compared to other homogenizers with similar structural design (e.g., U.S. Pat. No. 6,398,402), the custom blade core of the present invention spins and draws and forces food into the toothed surfaces of the custom cap. The custom o-ring seals between the custom cap and the custom cup which may be clear for visualization of homogenization progress and results. The homogenizer rotor may be made of any thermoplastics, including, but not limited to, polyamide (PA), Acrylanitrilebutadienestyrene (ABS), Polycarbonate (PC), High Impact Polystyrene (HIPS), and Acetal (POM).

In some embodiments, the homogenizer assembly 570 may be designed and modified for different homogenization mechanisms for different types of test samples, to meet specific requirements such as adding mechanical help to break up food, including grinding, cutting, blending, abrading or mixed movements. In some aspects, the homogenizer may include means (e.g., a stator and a corer) for increasing the agitation of the homogenizer. The homogenizer may have a "star knob" style handle which can be twisted to help for coring. The handle of stator/corer may be designed as herb grinder (textured band around edge); or pill crusher (with 3 flowerette knob); or pill crusher (with two winged knob). In other aspects, the stator/corer may by an object stator (e.g., 1 mm thick), PPE syringe corer, fine microplane, coarse microplane, and pulverizor, bead beating (marble agitator or steel ball agitator). In other embodiments, a homogenizer may be a hybrid with mixed processes to dissociate the test sample, for example by grinding and blending.

In some embodiments, the motor 510 can be a commercially available motor, for example, Maxon motor systems: Maxon RE-max and/or Maxon A-max (Maxon Motor ag, San Mateo, Calif., USA).

In some embodiments, a gear train or a drive may be used to connect the motor 510 to the homogenizer assembly 570. A gear train and/or a drive may allow the motor 510 to be packaged so it does not interfere with the ability of the food corer 200 to introduce food sample to the homogenizer assembly 570 while allowing the homogenizer stator 230 to be driven from above, and not require a liquid tight seal during operation. A label/final fluid seal 211 is provided by the applied label or other removable seal proximal to the area surrounding the stator cap 640. The gear train or the drive may also allow the power from the motor 510 to take 2 right angle turns and is therefore critical to a particular combination of user experience of the detection device 100 and functional requirement for the disposable test cup 300.

The test sample will be processed in an extraction buffer for protein extraction and allergen retrieval. In some embodiments, the extraction buffer may be optimized for increasing protein extraction. The extraction buffer may contain different agents for different test samples, such as those disclosed in Applicants' PCT Application Serial No. PCT/US2014/062656, the contents of which are incorporated herein by reference in their entirety.

In accordance with the present invention, a means for driving and controlling the flow of the processed sample solution and mixing said extraction solution with one or more detection signal molecules is provided. In some embodiments, the means may be a vacuum system or an external pressure. As a non-limiting example, the means may be a platen (e.g., a welded plastic clamshell) configured to being multifunctional in that it could support the axis of the gear train and it could provide the pumping (sealed air channel) for the vacuum to be applied from the pump to the test cup port 214 on the cup lid assembly 210 of the disposable test cup 300.

Figure 12A:
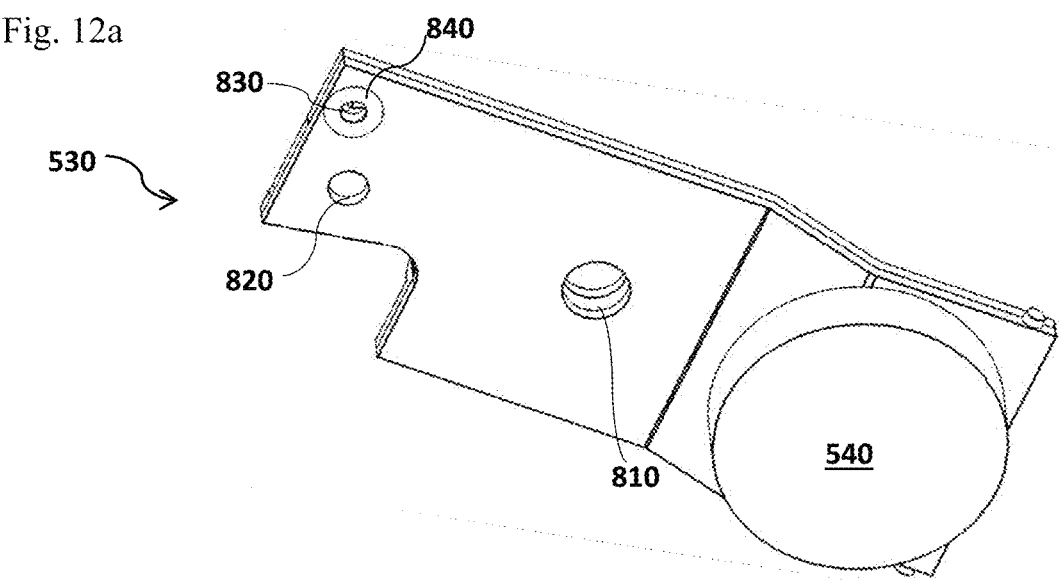
FIG. 12a is a bottom view of the gear train/drive platen 530 and FIG. 12b is a top view of the gear train/drive platen 530.
Figure 12B:
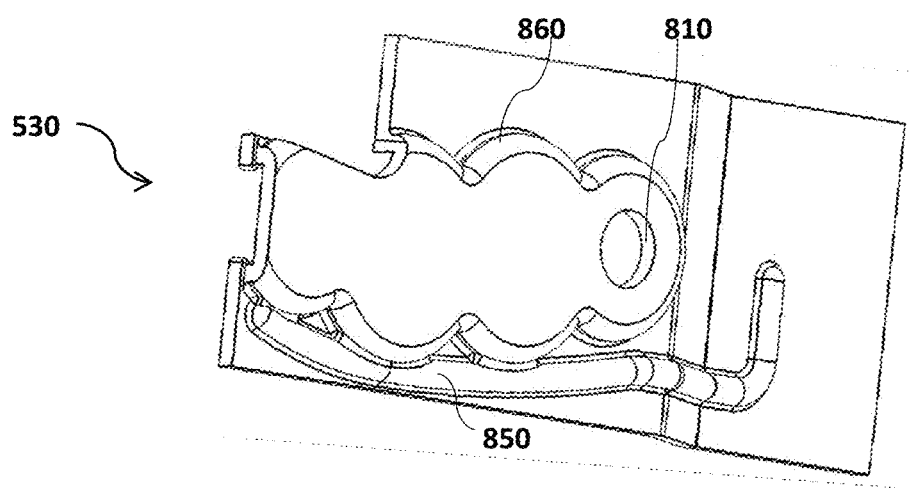

Referring to FIG. 12, a gear train/drive platen 530 may have a underside to which a pump (e.g., Piezo micropump) 540 is connected; and a topside which is provided with a vacuum duct 850 that is connected to the test cup port 214 (not shown) on the top of the cup lid assembly 210 (not shown) of the disposable test cup 300; and air channels 860. A gear train/motor port 810 which is configured for connection to the gear train or the drive that is connected to the motor 510 (not shown) and the homogenizer assembly 570 (not shown). A gear train/cup port 830 at the edge of the gear train/drive platen 530 is surrounded by a vacuum gasket 840 which seals the connection between the test cup port 214 (not shown) on the top of the cup lid assembly 210 and the gear train/cup port 830. The flow control port 820 provides a flow control of the extraction protein solution from the cup body 220 (not shown) to the reaction chambers 223 (not shown) with active feedback from the optical assembly 520 (not shown), or alternative optical assembly 1100 (not shown, illustrated in FIG. 14) or absorbance measurement assembly 1200 (not shown, illustrated in FIG. 15), or by fluid mechanical means such as a small orifice or hydrophobic membrane.

The pump 540, such as piezoelectric micro pump (Takasago Electric, Inc, Nagoya, Japan) may be used to control and automatically adjust the flow to a target flow rate. The flow rate of a pump is adjustable by changing either the driver voltage or drive frequency. The pump 540 shown in FIG. 12 is a representation of piezo pumps currently on the market that have specifications that indicate they could be suitable for the aliquot function required to bring filtered sample solution into the two reaction chambers 223. The pump 540 may be a vacuum pump or other small pumps designed for laboratory use such as KBF pumps (KNF Neuberger, Trenton, N.J., USA).

The vacuum gasket 840 provides a seal between the gear train/drive platen 530 and the test cup port 214 on the top of the cup lid assembly 210. In some embodiments, the vacuum gasket 840 could also be incorporated into the disposable test cup 300 to increase reliability of the detection device 100. The air channel 860 could also be executed with discrete tubing and fittings. The sample flow tube 221 will be isolated from the fluid channel 215 and reaction chambers 223 such that evaporation of the buffer solution will not prematurely dissolve the reactants by means such as a cap, a duckbill valve, an umbrella valve, a cone valve, X-Fragm (Minivalve) or similar arrangement. Opening pressures of any such valve must be controlled to open during operation but not during storage/shipment due to expansion of the air in the cup.

Figure 13:
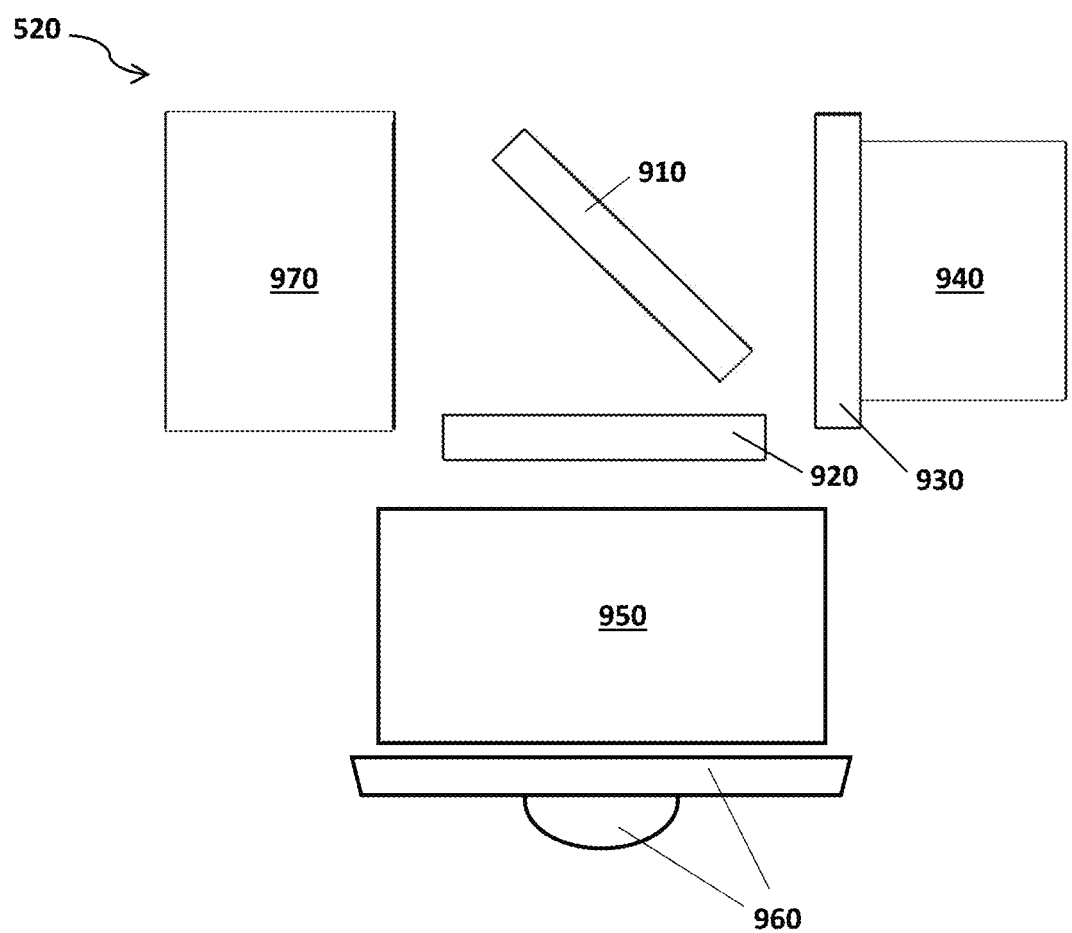
FIG. 13 illustrates one optical assembly 520 of the detection device 100.

In accordance with the present invention, as shown in FIG. 13, the reaction chambers (i.e., the allergen analytical chamber and the total protein control chamber) are connected with an optical assembly 520 of the detection device 100. The optical assembly 520 comprises a dichroic filter 910, an excitation filter 920 and an emission filter 930, a photodiode or a photomultiplier tube (PMT) 940 and light emitting diodes (LEDs) or a diode laser 950 (e.g. Avago LED and Luxeon Rebel LED) held by a LED housing 960. The LEDs or the diode laser 950 provide light of an excitation wavelength appropriate to excite the fluorophore of signaling polynucleotides. LEDs may have different shapes, e.g. a bulb or a plate. The light paths of the LEDs or the diode laser are directed into the analytical chamber 970. The analytical chamber 970 is one of the reaction chambers 223 (shown in FIG. 3). The emission filter 930 allows only the wavelength of interest to pass through from the fluorescence emitted from the analytical chamber 970 for detection by the photodiode or PMT 940. In this configuration, the dichroic filter 910 and the emission filter 930 are arranged in a particular angle from 30° to 60°. In one aspect, the angle between may be 45°. Signals from the detector (e.g., a spectrometer and a camera) may be converted to digital signals or processed as analog signals, and the amount of allergen corresponding to the signal is indicated in a corresponding display window 60 (not shown, see FIG. 1b), which functions as a user interface screen.

Figure 14:
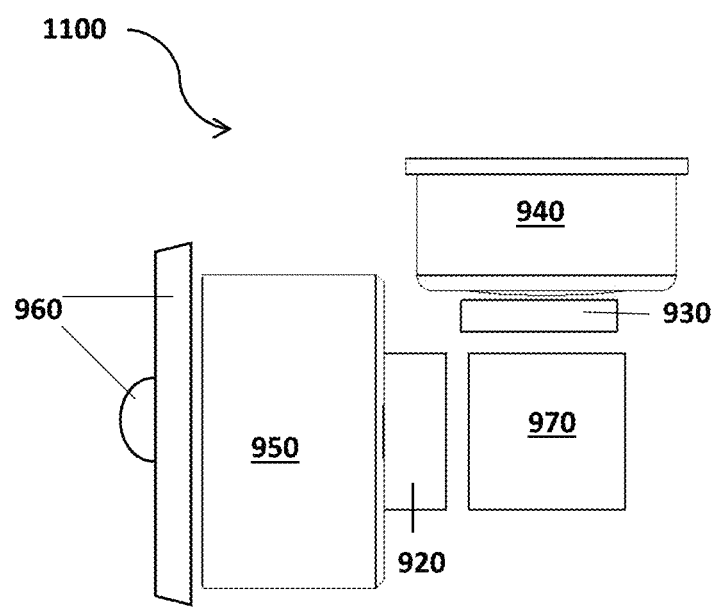
FIG. 14 illustrates an alternative embodiment of the optical assembly 1100.

In accordance with the present invention, the optical system may be assembled into an alternative optical assembly 1100 configuration as illustrated in FIG. 14. Again the excitation is provided by LEDs or by a diode laser 950 held in a LED housing 960 shining light at the excitation wavelength of the fluorophore that labels the signal polynucleotides through an excitation filter 920 which is a low pass filter that further ensures the wavelength is as required. The light illuminates the detection sample in the analytical chamber 970 and the sample emits light at a different wavelength which is filtered by an emission filter 930 and detected by the photodiode or PMT 940. In this embodiment, the excitation filter 920 and the emission filter 930 are arranged in a particular angle from 10° to 160°. In one aspect, the angle may be 90°.

Figure 15:
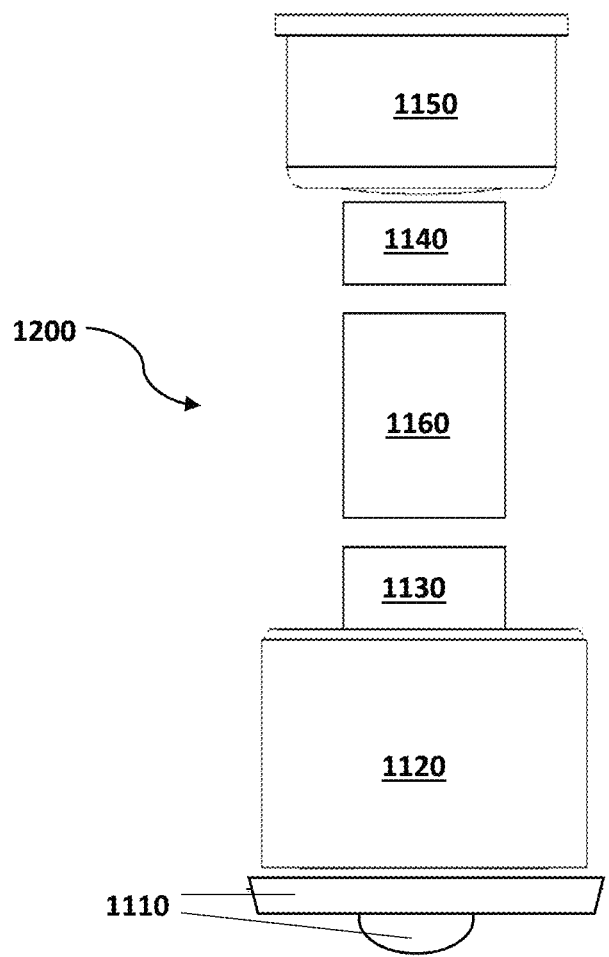
FIG. 15 illustrates an absorbance detection assembly 1200 of the detection device 100.

FIG. 15 illustrates one embodiment of the absorbance measurement assembly 1200. An absorbance assembly LED or diode laser 1110 held by an absorbance assembly LED housing 1120 shines light at the correct wavelength for the absorbance of the chemicals in use, i.e. 600 nm for pyrogallel red. The light emitted from the LEDs or the diode laser 1110 is further refined by the first absorbance filter 1130 and then passes through a control chamber 1160. The control chamber 1160 is one of the reaction chambers 223. The light then passes through the second absorbance filter 1140 which isolates the desired wavelength from any ambient light, and is detected by the absorbance assembly photodiode or PMT 1150. The signal is processed either as an analog signal or digitized and analyzed against a threshold after further filtering and processing.

The LEDs integrated into the optical assembly 520 (or 1100, or 1200) may be an Avago LED (Avago Technologies, San Jose, Calif., USA), or a Luxeon Rebel LED (Luxeon LEDs, Ontario Canada).

The above described optical assembly 520, the alternative optical assembly 1100 and the absorbance measurement assembly 1200 are illustrative examples of certain embodiments. In some embodiments they might have different configurations and/or different components. In some embodiments, the optical assembly or the alternative optical assembly may be configured together with an absorbance measurement assembly. In such configurations, some of the components, such as reaction chambers, excitation sources (LEDs or a diode laser); detectors (e.g. photodiode or PMT), filters and/or other components might be shared by the assemblies.

Figure 16:
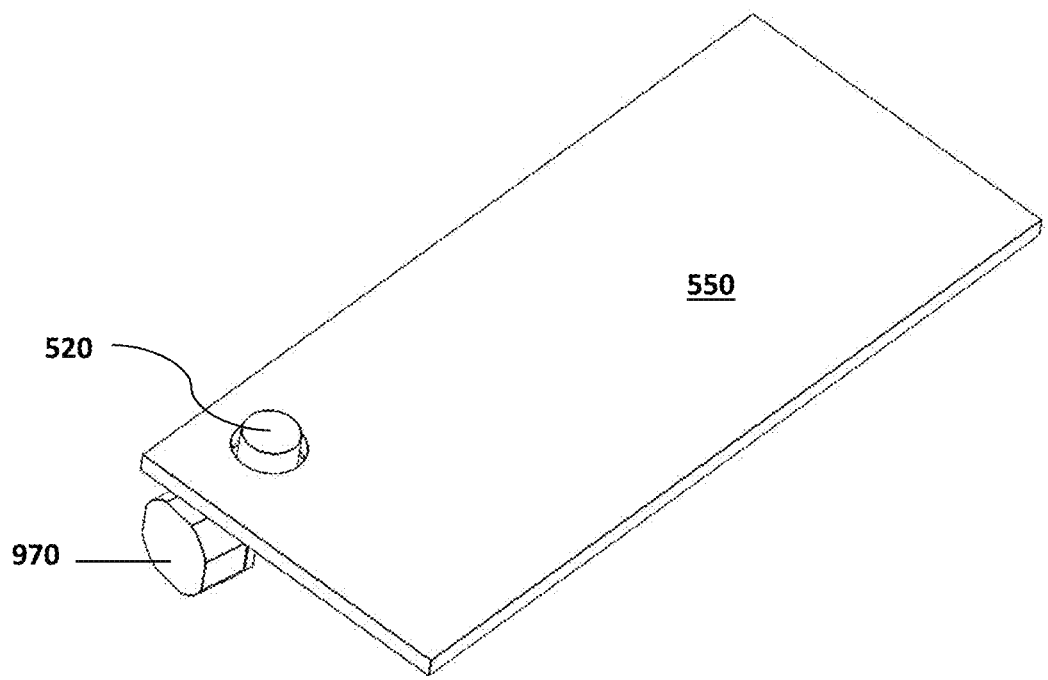
FIG. 16 illustrates a Printed Circuits Board (PCB) 550 which is connected to the optical assembly 520. The main control PCB contains motor and pump/actuator control electronics.

As shown in FIG. 16, a Printed Circuit Board (PCB) 550 is connected to the optical assembly 520 and the analytical chamber 970 (one of the reaction chambers 223). The PCB 550 may be configured to be compact with the size of the detection device 100 and at the same time, may provide enough space to display the testing result.

In accordance, the test result may be displayed with back lit icons, LEDs or an LCD screen, OLED, segmented display or on an attached mobile phone application. The user may see an indicator that the sample is being processed, that the sample was processed completely (total protein indictor) and the results of the test. The user may also be able to view the status of the battery and what kind of cartridge he/she placed in the device (bar code on the cartridge or LED assembly). The results of the test will be displayed, for example, as 1) actual number ppm or mg; or 2) binary result yes/no; or 3) risk analysis—high/medium/low or high/low, risk of presence; or 4) range of ppm less than 1/1-10 ppm/more than 10 ppm; or 5) range of mg less than 1 mg/between 1-10 mg/more than 10 mg. The result might also be displayed as number, colors, icons and/or letters. In accordance with the present invention, the detection device 100 may also include other features such as means for providing power supply and means for providing a control of the process. In some embodiments, one or more switches are provided to connect the motor, the micropump and/or the gear train or the drive to the power supply. The switches may be simple microswitches that can turn the detection device on and off by connecting and disconnecting the battery.

The power supply 560 may be a Li-ion AA format battery or any commercially available batteries that are suitable for supporting small medical devices such as Rhino 610 battery, Turntigy Nanotech High dischargeable Li Po battery, or a Pentax D-L163 battery.

Allergen Detection Testing

In another aspect of the present invention, there is provided an allergen detection testing using aptamer-based signal polynucleotides as allergen detection molecules.

Sampling

To provide a reliable and sensitive result from an allergen detection testing, a right size of a testing sample is important. The inventors of the present invention developed a sampling mechanism that can collect a test sample effectively and non-destructively for fast and efficient extraction of allergen proteins for detection.

A sized portion of the test sample can be collected using, for example, a food corer 200 illustrated in FIG. 2. The sample pickup (e.g., food corer 200) can measure the size and collect a rightly sized sample which can provide enough protein extraction for the detection testing. The sized portion may be ranged from 0.1 g to 1 g food sample. Furthermore, the food corer 200 may pre-process the collected test sample by cutting, grinding, blending, abrading and/or filtering. Pre-processed test sample will be introduced into the sample processing cup body 220 for homogenization and allergen protein extraction. As illustrated in FIGS. 1b, 3 and 4, the food corer 200 may be inserted into the food corer port 213 on the top of the cup lid assembly 210 and releases the test sample into the disposable test cup 300.

The collected test sample is processed in an extraction buffer. In some aspects, an extraction buffer is present in the cup body 220 and may be mixed with the test sample by the homogenizer assembly 570. In other aspects, the extraction buffer may be released into the cup body 220 from a local region (e.g., at the bottom of the cup 220) by manual plunging or automatically release from the storage place to the cup chamber. The test sample and the extraction buffer will be mixed together by the homogenizer assembly 570 and the sample being homogenized.

The extraction buffer may be universal target extraction buffer that can retrieve enough target proteins from any test sample and be optimized for maximizing protein extraction. In some embodiments, the formulation of the universal protein extraction buffer can extract the protein at room temperature and in minimal time (less than 1 min). The same buffer may be used during food sampling, homogenization and filtering. The extraction buffer may be PBS based buffer containing 10%, 20% or 40% ethanol, or Tris based buffer containing Tris base Ph8.0, 5 mM MEDTA and 20% Ethanol, or a modified PBS or Tris buffer. Some examples of modified PBS buffers may include: P+ buffer and K buffer. Some examples of Tris based buffers may include Buffer A+, Buffer A, B, C, D, E, and Buffer T. A detailed description of each modified buffer is disclosed in the PCT patent application No. PCT/US2014/062656; the content of which is incorporated herein by reference in its entirety.

The volume of the extraction buffer may be from 0.5 mL to 3 mL, which has been determined to be efficient and repeatable over time and in different food matrices.

In accordance with the present invention, the test sample is homogenized and processed using a homogenizer (e.g. the homogenizer assembly 570) that has been optimized with high speed homogenization for maximally processing the test sample. In some aspects, a filtering mechanism may be linked to the homogenizer. The homogenized sample solution is then driven to flow through a filter processing to further extract allergen proteins, lowering the amount of other molecules extracted from the test sample. A filter membrane such as cell strainer from CORNING (CORNING, NY, USA) may be connected to the homogenizer. The filter pores can be between 0.2 µm to 600 µm. The filter can be made from any low binding material, including, but not limited to, PES (Polyethersulfone), PCTE (Polycarbonate) or PVDF (polyvinylidene difluoride).

In some aspects, the sampling procedure may reach effective protein extraction in less than 1 minute. In one aspect, speed of digestion may be less than 2 minutes including food pickup, digestion and readout. Approximately, the procedure may be 15 seconds, 30 seconds, 45 seconds, 50 seconds, 55 seconds or 1 minute.

Sensors and Detection Molecules

Extracted allergen proteins may be mixed with one or more detection molecules that are specific to one or more allergens of interest and the interaction between allergen protein extraction and detection molecules will generate a signal which indicates the presence, or absence or the amount of one or more allergens in the test sample. As used herein, the term "detection molecule" or "allergen detection molecule" refers to any molecule which is capable of, or does, interact with and/or bind to one or more allergens in a way that allows detection of such allergen in a sample. In one aspect of the present invention, the detection molecules are nucleic acid molecules based signal polynucleotides.

In accordance with the present invention, the detection molecules may be signal polynucleotides which use aptamers as core sequences with various reporter molecules such as fluorophores. As used herein, the term "aptamer" refers to a nucleic acid species that has been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The binding specify and high affinity to target molecules, the sensitivity and reproductively at ambient temperature, the relatively low production cost, and the possibility to develop an aptamer core sequence that can recognize any protein, ensure an effective but yet simple detection assays for the sensors of the detection device as described herein.

In accordance with the present invention, aptamer molecules that can be used as detection molecules in the analytical chamber 970 may be aptamers described in applicants' relevant patent applications including U.S. Provisional Application Ser. No. 62/026,361, filed on Jul. 18, 2014; U.S. Provisional Application Ser. No. 62/009,958, filed on Jun. 10, 2014; U.S. Provisional Application Ser. No. 61/991,068, filed on May 9, 2014; U.S. Provisional Application Ser. No. 61/938,528, filed on Feb. 11, 2014; U.S. Provisional Application Ser. No. 61/896,399, filed on Oct. 28, 2013; and PCT Application Serial No. PCT/US2014/062656, filed on Oct. 28, 2014; the content of each of which is herein incorporated by reference in their entirety.

In addition to aptamers based signal polynucleotides, detection molecules used in the detection device 100 may be any molecule or molecules which are capable of association or binding to one or more allergens such as antibodies and variants thereof. The antibodies detectors may be polyclonal and/or monoclonal antibodies.

In accordance with the present invention, the detection molecules used in the detection device 100 are further labeled. In some aspects, the detection molecules are labeled with fluorophores and quenchers at each end of the detection molecules. When the detection molecule is in close state, the fluorophore and the quencher is brought together and the fluorescent is quenched ("turned-off"). When a target allergen is recognized and bound to the detection molecule, the conformational change will open the closed structure and the fluorophore and the quencher is separate. The fluorescence is no longer quenched and is "turned on", which generates a fluorescent signal. The optical assembly 520 or the alternative optical assembly 1100 of the detection device 100 is configured to capture such fluorescent signals from the binding of allergens to the detection molecules.

Allergen families that can be detected using the detection system and device described herein include allergens from foods, the environment or from non-human proteins such as domestic pet dander. Food allergens include, but are not limited to proteins in legumes such as peanuts, peas, lentils and beans, as well as the legume-related plant lupin, tree nuts such as almond, cashew, walnut, Brazil nut, filbert/hazelnut, pecan, pistachio, beechnut, butternut, chestnut, chinquapin nut, coconut, ginkgo nut, lychee nut, macadamia nut, nangai nut and pine nut, egg, fish, shellfish such as crab, crawfish, lobster, shrimp and prawns, mollusks such as clams, oysters, mussels and scallops, milk, soy, wheat, gluten, corn, meat such as beef, pork, mutton and chicken, gelatin, sulphite, seeds such as sesame, sunflower and poppy seeds, and spices such as coriander, garlic and mustard, fruits, vegetables such as celery, and rice. The allergen may be present in a flour or meal, or in any format of products. For example, the seeds from plants, such as lupin, sunflower or poppy can be used in foods such as seeded bread or can be ground to make flour to be used in making bread or pastries.

In some embodiments, detection molecules for 8 major food allergens (i.e. wheat, egg, milk, peanuts, tree-nuts, fish, shell-fish and soy) may be provided as disposables. In one aspect, constructs of the detection molecules may be stored with MgCl, or buffer doped with KCl. MgCl keeps constructs closed tightly, while KCl opens them slightly for bonding.

Detection System

The mixture of allergen protein extraction and detection molecules is analyzed in the analytical chamber 970. As described above, a detection molecule (e.g., aptamer based signaling polynucleotide) has a close secondary sequence in which the fluorophore at one end of the molecule is brought together with the quencher at the other end of the molecule, causing fluorescent signal is quenched. The binding of allergen in the protein extraction causes the conformational changes of the second sequence of the detection molecule, causing the separation of the fluorophore from the quencher. A fluorescent signal will release from the un-quenched fluorophore. According to the present invention, an optical assembly 520 or the alternative optical assembly 1100 can detect such signal and convert the detected signals to digital signals, or compare analog signals to thresholds which are used to indicate the user the presence, or absence, or the amount of allergen in the test sample.

Fluorophore can be at a different wavelength from 405, 635-650, to 780 nm. Flourophores being excited by lights at this range would allow for inexpensive laser or LED illumination. A printed circuit board (PCB) 550 may be used to convert the fluorescent signals into digital signals or comparing analog signals to thresholds for displaying the readouts of the detection testing to the user. In some embodiments, a polystyrene window can be designed for reading, as fluorescent readings are very precise and repeatable in polystyrene well plate.

In the process of the detection testing, the total protein of the test sample is determined and the signal from the allergen detection reaction is compared to the total protein absorbance. As discussed above, the control chamber 1160 (one of the reaction chambers 223) on the top of the cup lid assembly 210 receives a portion of the extraction protein solution in parallel from the flow tube 221 and the fluid channel 215, and the solution is mixed with the total protein indication molecules (e.g., Pyrogalbl Red Molybdate, PRM) present in the control chamber 1160 (one of the reaction chambers 223). The absorbance at different light wavelengths (e.g., 450 nm, 600 nm and 720 nm) is detected by the absorbance detection assembly 1200 of the detection device 100, which is used to indicate the total protein from the test sample. The total protein is a measurement that will assess if enough food was sampled and if the sample was homogenized to an acceptable degree.

In some embodiments, the total protein indication molecules (e.g., Pyrogalbl Red Molybdate, PRM) may be pre-prepared in solution and will be dried and provided to the control chamber 1160 (one of the reaction chambers 223) on the top of the cup lid assembly 210.

In addition to above described detection method comprising fluorescence and absorbance measurement, the detection mechanism may be based on a chemiluminescence measurement, a colorimetric measurement, a pH measurement, a measurement of dissolved oxygen, a redox measurement and/or other suitable measurement.

Creating an Allergen Standard

The detection molecules (i.e., SPNs) for each allergen are tested on pure protein dilutions and the standard curve is determined for each allergen. As listed in Table 1, common allergens are tested:

TABLE 1

| Allergen | Pure protein dilutions |
| --- | --- |
| Peanut | peanut flour |
| Egg | dried egg whites |

TABLE 1-continued

| Allergen | Pure protein dilutions |
| --- | --- |
| Milk | dried non-fat skim milk |
| Soy | soy flour |
| cashew | cashew mill |
| wheat | Gluten (sigma) |
| Fish | Fish para-albumin (homogenized fresh fish) |
| Crustacean | homogenized crab meat |

The curve will be tested from 100 mg/mL (100,000 ppm) to 0.0001 mg/mL (0.1 ppμ). Once the binding curve is determined the OD for the threshold will be determined. As a non-limiting example, if the threshold for detection should be 10 ppm and the OD for 10 ppm of peanut is 2500 OD, such OD is determined as the threshold. The standard curve and the threshold for each allergen may be used for signal analysis and comparison during an allergen detection testing.

User Interface

In some embodiments, the detection system may further comprise a user interface system allowing users to receive results from the detection device remotely. The user interface system may include a software application. The software application may be housed in the detection device or externally. When external to the chemical sensor device the software may be configured to run on a smartphone, a smartwatch, a personal computer (PC), a laptop computer, a tablet computer, other medical devices and/or other device. The software application may be used for operations such as, but not limited to receiving data from the device, analyzing data, reporting data and storing data. The software application may store, analyze and share data at the device level, localized level and/or at a cloud level. As used herein, a cloud refers to one or more servers that operate remotely and may be accessed via the internet. In some embodiments, the software application may be operated through an internet browser.

In some embodiments, the detection device may comprise firmware that allows communication between the software application and the device. The software application may communicate with the detector device via a wireless or a wired transmitter. The wireless transmitter may be e.g. a BLUETOOTH® transmitter.

The application software may be used for reporting data as readouts, graphs, graphical or numerical manifestation and/or alerts. The alerts may be readouts, tonal or vocal alerts. The user may view, store and/or share data. The software application may be used to share and view data among users. The users may enter customized information to the software application and use the data to gain personalized alerts. As a non-limiting example, a mother may enter data related to her children's allergies, and upon detection of certain allergens, the smartphone may alert by indicating the names of children that are in the risk of having an allergic reaction. The software application may pass the data across a network using standard communication protocols, such as the internet. The cloud system may provide automated alerts and/or predictive alerts based on the received and processed data. As an example, xxx Cloud systems for receiving, processing, storing, distributing and sharing data are discussed in Jeong et al. (US 2013/0160006), Chen et al. (US 2013/0282227), Williams (US 2014/0257833), Kain et al. (US 2013/0274148) and Wu et al. (US 2013/0317381), the contents of which are incorporated herein by reference in their entirety.

Applications

The detection systems, devices and methods described herein contemplate the use of nucleic acid-based detector molecules such as aptamers for detection of allergens in food samples. The portable devices allow a user to test the presence or absence of one or more allergens in food samples that the user is allergic to. Allergen families that can be detected using the device described herein include allergens from legumes such as peanuts, tree nuts, eggs, milk, soy, spices, seeds, fish, shellfish, wheat gluten, rice, fruits and vegetables. The allergen may be present in a flour or meal. The device is capable of confirming the presence or absence of these allergens as well as quantifying the amounts of these allergens.

In a broad concept, the detection systems, devices and methods described herein may be used for detection of any protein content in a sample in a large variety of applications in addition to food safety, such as, for example, medical diagnosis of diseases in civilian and battlefield settings, environmental monitoring/control and military use for the detection of biological weapons. In even broad applications, the detection systems, devices and methods of the present invention may be used to detect any biomolecules which nucleic acid-based detector molecules bind. As some non-limiting examples, the detection systems, devices and methods may be used on the spot detection of cancer markers, in-field diagnostics (exposure the chemical agents, traumatic head injuries etc.), third-world applications (TB, HIV tests etc.), emergency care (stroke markers, head injury etc.) and many others.

As a non-limiting example of applications, the detection systems, devices and methods of the present invention can detect and identify pathogenic microorganisms in a sample. Pathogens that can be detected include bacteria, yeasts, fungi, viruses and virus-like organisms. Pathogens could cause diseases in animals and plants; contaminate food, water, soil or other sources; or is used as biological agents in military fields. The device is capable of detecting and identifying these pathogens.

Another important application includes the use of the detection systems, devices and methods of the present invention for medical care, for example, to diagnose a disease, to stage a disease progression and to monitor a response to a certain treatment. As a non-limiting example, the detection device of the present invention may be used to test the presence or absence, or the amount of a biomarker associated with a disease (e.g. cancer) to predict a disease or disease progression. The detection systems, devices and methods of the present invention are designed to analyze a small amount of test sample and can be implemented by a user without extensive laboratory training.

Other expanded applications outside of the field of food safety include in-field use by military organizations, testing of antibiotics and biological drugs, environmental testing of products such as pesticides and fertilizers, testing of dietary supplements and various food components and additives prepared in bulk such as caffeine and nicotine, as well as testing of clinical samples such as saliva, skin and blood to determine if an individual has been exposed to significant levels of an individual allergen.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

EXAMPLE

Example 1: Sampling Mechanisms

A variety of tools were tested for picking up and collecting different types of food samples. As indicated in Tablet, different parameters and mechanisms were considered in designing the optimized sample pickup.

TABLE 2

| Mechanisms | Soup | Ice Cream | Croutons | Meat | Frosting | Cake | Marshmallow | Chocolate | Whipped Cream |
|---|---|---|---|---|---|---|---|---|---|
| Homogenizing generator | x | x | x | x | X | x | x | x | X |
| Blender/emulsifier | x | x | x |  | X | x |  |  |  |
| Knife/utensil | x | x |  | x | X | x | x |  | X |
| Coring punch |  |  |  | x |  |  |  |  |  |
| Drill/auger | x | x |  |  |  |  |  |  |  |
| Syringe punch | x |  |  | x | X | x |  |  |  |
| Nibble (multiple) |  |  | x |  |  |  |  | x |  |
| Garlic press (knife edge mesh) | — | — |  |  | X |  |  |  |  |
| Cheese grater (rotary) | — | — | x |  |  |  |  |  |  |
| Pepper grinder | — | — |  |  |  |  |  |  |  |
| Meat grinder | — | — |  | x | — |  |  |  |  |
| Herb grinder | — | — |  |  |  |  |  |  |  |

TABLE 2-continued

| Mechanisms | Soup | Ice Cream | Croutons | Meat | Frosting | Cake | Marshmallow | Chocolate | Whipped Cream |
|---|---|---|---|---|---|---|---|---|---|
| Pill crusher | — | — | x | | | | | | |
| Slap chop | — | — | x | | | | | x | |
| Microplane | | | x | | | | | x | |
| Biopsy needle (multiple) | | | | x | X | x | x | | |
| Oil drill | x | x | | | | | | | |
| Active shaver | — | | x | | | | | x | |
| Food scale | x | x | x | x | X | x | x | x | X |
| Integrated strain gauge | x | x | x | x | X | x | x | x | X |
| Flex cup/spoon | | | — | | | | | x | |
| Spring scale spoon | x | x | | | | | | x | |
| Volume graduations | x | x | | | | | | | |
| MACs (a food mill) | x | x | | | | | | | |

Similarly, for each tool and mechanism, its effectiveness in facilitating the process of test sample was tested and summarized in Table 2.

TABLE 3

| Mechanisms | Measure | Cut | Pick-up | Pre-process | Release | Homogenize |
|---|---|---|---|---|---|---|
| Homogenizing generator | | | | | | X |
| Blender/emulsifier | | | | | | X |
| Knife/utensil | | x | X | ? | | |
| Coring punch | x | x | X | x | | |
| Drill/auger | | x | | x | | |
| Syringe punch | x | x | X | | x | |
| Nibble (multiple) | x | X | | x | | |
| Garlic press (knife edge mesh) | | | | X | | |
| Cheese grater (rotary) | | | | x | X | |
| Pepper grinder | | | | x | X | |
| Meat grinder | | | | x | x | |
| Herb grinder | | | | x | X | |
| Pill crusher | | | | X | X | |
| Slap chop | | X | | x | | |
| Microplane | | X | | | | |
| Biopsy needle (multiple) | x | x | X | X | | |
| Oil drill | | X | | X | | |
| Active shaver | | | x | | ? | |
| Food scale | x | | | | | |
| Integrated strain gauge | | x | | | | |
| Flex cup/spoon | X | | | | | |
| Spring scale spoon | x | | | | | |
| Volume graduations | x | | | | | |
| MACs (a food mill) | | | | | | X |

In the process of developing a precise and speed sampling mechanism, GentalMACS homogenizer was used for comparison. The goal of the testing is to develop a low power but high speed homogenizer. The designed homogenizer with a stator and a rotor can process various types of food matrices effectively, including hard chocolate chunk, chicken meat and soft frosting.

What is claimed is:

1. A portable allergen detection system comprising:
   (a) a food pickup corer for picking-up and/or collecting a test sample, said food pickup corer comprising a sample collection tube having a proximal end and a distal end, and a plunger inside the sample collection tube;
   (b) at least one disposable test cup or cup-like container that comprises a cup lid assembly and a cup body having a wider distal end connected to the cup lid assembly and a proximal base, configured for receiving and processing the test sample; and
   (c) a detection device configured for detecting the presence or absence of one or more allergens in the test sample; and
   wherein the cup lid assembly comprises three ports on the top cap of the cup lid assembly: a first port for holding a food corer, a second port through which a homogenizer is assembled, and a third port for collection to a flow controlling means for driving and controlling the flow rate of the processed sample solution during the allergen detection; a fluid channel for conveying the processed sample solution from the cup body to reaction chambers; and two reaction chambers on the top cap of the cup lid assembly for detection of said one or more allergens in the test sample.

2. The allergen detection system of claim 1, wherein the food pickup corer has a distal portion provided with a corer top cap at the distal end, a proximal portion provided with the sample collecting tube, a grip for handling the corer which is connected to the sample collecting tube, and the plunger inside the sample collecting tube which has a distal end connected to the top cap and a plunger tip at the proximal end,
   wherein the proximal plunger tip can protrude out from the sample collecting tube for picking up the test sample.

3. The allergen detection system of claim 2, wherein the food pickup corer is further provided with a means for weighing the test sample being picked up.

4. The allergen detection system of claim 1, wherein the two reaction chambers consist of one allergen analytical chamber wherein detection molecules specific to the one or more allergens are present, and the other total protein control chamber wherein total protein indication molecules are present, wherein the allergen analytical chamber and the control chamber are arranged in parallel and receive the processed sample solution simultaneously.

5. The allergen detection system of claim 4, wherein the cup lid assembly further comprises, (a) a flow tube through which the processed sample solution is flowed from the cup body to the two reaction chambers; and (b) a flow tube cap and filter assembly in the cup lid assembly for further filtering large particles in the processed sample solution and preventing humidification of the molecules in the two reaction chambers.

6. The allergen detection system of claim 4, wherein the detection molecules are aptamer based signal polynucleotides (SPNs) which are labeled with a fluorophore and a quencher at each end, and wherein the total protein indication molecules are Pyrogalbl Red Molybdate (PRM).

7. The allergen detection system of claim 1, wherein the homogenizer assembled comprises a homogenizer rotor and a stator that are inserted into the cup body through the second port (b) on the top of the cup lid assembly, wherein the distal caps of the homogenizer rotor and stator are connected to the second port and the proximal portions of the homogenizer rotor and stator extend to the cup body.

8. The allergen detection system of claim 1, wherein the cup body is configured for receiving the test sample collected by the food corer and processing the test sample using the homogenizer assembled through the second port on the top of the cup lid assembly, and wherein the cup body contains a volume of an extraction buffer which is used for dissociating the test sample and extracting allergen proteins.

9. The allergen detection system of claim 1, wherein the detection device comprises:

(a) an external housing configured for providing support for the components of the detection device consisting of a housing cover and a housing base;

(b) a first part that can be opened for insertion of the disposable test cup or cup-like container; and (c) components for detecting said one or more allergens including:

(i) means for driving and controlling a homogenizer;

(ii) means for driving and controlling the flow of the processed sample solution during the process of the allergen detection testing;

(iii) an optical assembly for providing fluorescence excitation and for filtering of fluorescence emission; and providing light sources for protein absorbance at certain wavelength;

(iv) means for detecting fluorescence emissions from the detection reaction between said one or more allergens and the detection molecules, and for collecting the protein absorbance; and digitizing detected signals;

(v) a display window for receiving the detected signals and indicating the presence and/or absence of the allergen in the test sample; and/or (vi) a power supply.

10. The allergen detection system of claim 9, wherein the first part 00 is a drawer assembly or a hinged door that can be lifted.

11. The allergen detection system of claim 10, wherein the first part (b) is a drawer assembly that comprises an open well for inserting the disposable test cup or cup-like container and a drawer frame, the drawer frame comprising one chimb on each side of the drawer frame, respectively, wherein the drawer assembly can be pulled out when implementing an allergen detection testing and slide back into the housing, and wherein the housing base comprises one groove on each bottom side, respectively, which is configured for sliding the drawer assembly.

12. The detection system of claim 11, wherein the external housing comprises an alignment on the top front of the housing for aligning the disposable test cup or cup-like container during the process of the allergen detection testing.

13. The detection system of claim 7, wherein the homogenizer rotor is inside the homogenizer stator, and wherein the homogenizer assembly further comprises a coupling that couples the homogenizer stator and the rotor to a gearhead, and a gearhead for connecting the homogenizer to a gear train.

14. The detection system of claim 13, wherein the proximal end of the homogenizer stator is provided with one or more slots on the axis of the stator which extend to the cup body, and wherein the proximal end of the homogenizer rotor is provided with one or more blades which extend to the cup body.

15. The detection system of claim 14, wherein the homogenizer is further connected to a motor for driving and controlling the homogenization through the gearhead and the gear train.

16. The detection system of claim 9, wherein a vacuum micro pump is used as means for driving and controlling the flow of the extracted allergen protein solution.

17. The detection system of claim 9, wherein the optical comprises an excitation filter, an emission filter, a photodiode or a photomultiplier tube (PMT), a dichroic part and one or more LEDs, wherein the optical assembly is connected to the analytical chamber and the total protein control chamber in the cup lid assembly.

18. The detection system of claim 17, wherein the excitation and emission filters are arranged in an angle between 30° to 60°.

19. The detection system of claim 18, wherein the angle is 45°.

20. The detection system of claim 17, wherein the LED is held in a LED housing, and wherein the excitation filter and the emission filter are arranged in an angle between 10° to 160°.

21. The detection system of claim 20, wherein the angle is 90°.

22. The detection system of claim 17, wherein the detection device further comprises an absorbance measurement assembly which includes a LED or a diode laser held in a LED housing, one or more filters for isolating a desired light wavelength, and a photodiode or photomultiplier tube (PMT) for detecting the light absorbance.

23. The detection system of claim 9, wherein the power supply is a rechargeable or replaceable battery.

24. The detection system of claim 9, wherein the display is a Printed Circuits Board (PCB).

25. The detection system of claim 1, wherein the test sample is a food sample.

26. The allergen detection system of claim 7, wherein the disposable cup or cup-like container further comprises an additional control chamber on the top cap of the cup lid assembly and an air vent within the fluid channel, wherein the additional control chamber is used to measure non-specific background signals from an allergen detection assay, and wherein the air vent is used to block liquid flow between different chambers.

27. The allergen detection system of claim 8, wherein the cup body comprises a filter membrane which is aligned in parallel with the cup proximal base with a certain distance from the cup proximal base, wherein the reaction chambers are located at the bottom of the cup body and configured for receiving a test sample solution after being filtered by the filter membrane.

28. The allergen detection system of claim 27, wherein the disposable cup or cup-like container further comprises a valve at the bottom of the cup body for controlling the fluid flow to the reaction chambers, wherein the valve is selected from the group consisting of an umbrella valve, a duckbill valve, a one way-valve and a frangible seal.

29. The allergen detection system of claim 1 further comprising a small chamber attached to the cup body on the side wall of the cup body, wherein the cup body comprises a filter membrane, which is aligned in parallel with the side wall of the cup body with a certain distance from the side wall, and wherein the small chamber is configured for receiving a test sample solution after being filtered by the filter membrane.

30. The detection system of claim 1, wherein the homogenizer assembly comprises a homogenizer rotor which is welded to the second port on the top cap of the cup lid assembly, through a membrane seal.

\* \* \* \* \*